United States Patent
Dankwardt et al.

(10) Patent No.: US 6,426,402 B1
(45) Date of Patent: Jul. 30, 2002

(54) PEPTIDIC PROCOLLAGEN C-PROTEINASE INHIBITORS

(75) Inventors: Sharon Marie Dankwardt, Sunnyvale; Harold Edgar Van Wart; Keith Adrian Murray Walker, both of Los Altos, all of CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 09/459,201

(22) Filed: Dec. 10, 1999

Related U.S. Application Data

(60) Provisional application No. 60/111,661, filed on Dec. 10, 1998.

(51) Int. Cl.⁷ .................................................. C07K 5/08
(52) U.S. Cl. ........................ 530/331; 530/330; 514/18; 514/19
(58) Field of Search ..................... 514/18, 19; 530/331, 530/330

(56) References Cited

FOREIGN PATENT DOCUMENTS

| | | |
|---|---|---|
| EP | 0 084941 A1 | 8/1983 |
| FR | 2762315 A1 | 4/1997 |
| JP | 01 146896 | 6/1989 |
| JP | 08311096 A2 | 11/1996 |
| JP | 09 025293 | 1/1997 |
| WO | WO 92/22523 | 12/1992 |
| WO | WO 95/12612 | 5/1995 |
| WO | WO 96/33176 | 10/1996 |
| WO | WO 97/05865 | 2/1997 |
| WO | WO97/43251 A1 | 11/1997 |
| WO | WO97/49679 A1 | 12/1997 |
| WO | WO98/15525 A1 | 4/1998 |
| WO | WO98/22494 A2 | 5/1998 |
| WO | WO 98/55449 | 12/1998 |

OTHER PUBLICATIONS

Abstract of JP–09025293–A, 1997.*
Ewenson, et al., *Eur. J. Med. Chem.* vol. 27:3, pp 179–186 (1992), Synthesis and biological activity of peptide hydroxamate inhibitors of degradation of substance P analogues.

Chen, et al., *Bioorg. Med. Chem. Lett.*, vol. 2:12, pp1685–90 (1992), "One–pot synthesis of cathepsin inhibitors: $N^{\alpha}$–protected N–peptidyl–o–acetyl hydroxylamines catalysed by alcalase followed by lipase in anhydrous t–butanol".

Nikam, et al., *Tetrahedron Letters*, vol. 36:2, pp 197–200 (1995), "Synthesis of hydroxamic acids: Pd/BaSO4 as a new catalyst for the deprotection of o–benzyl hydroxamates".

Laufer, et al., *Eur. Journal of Biochemistry*, vol. 150:1 pp 135–140 (1985), "Inhibition of substance P degradation in rat brain preparations by peptide hydroxamic acids".

Fischer, et al., *Pharmazie*, vol. 38:4, pp 249–250 (1983), "N,O–Diacylhydroxylamines as Enzyme–Activated Inhibitors for Serine Proteases".

Hoffmann, et al., *Journal of Organic Chemistry*; vol. 29: pp 748–751 (1964), "A Peptide Synthesis via Hydroxamic Acids".

Fertala, et al., *J. Bio. Chem.* vol. 269, pp 11584–11589 (1994), Self–assembly into Fibrils of Collagen II by Enzymic Cleavage of Recombinant Collagen II.

* cited by examiner

*Primary Examiner*—Christopher S. F. Low
(74) *Attorney, Agent, or Firm*—Rohan Peries; Gloria Pfister

(57) ABSTRACT

This invention relates to compounds of Formula (I)

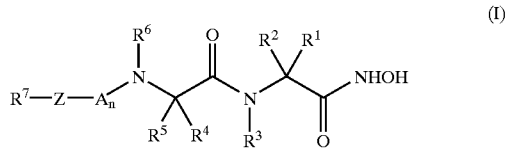

wherein $R^1$–$R^7$, A, Z and n are as described in the Summary of the Invention that are inhibitors of procollagen C-proteinase, pharmaceutical compositions containing them, methods for their use and methods for their preparation.

41 Claims, No Drawings

PEPTIDIC PROCOLLAGEN C-PROTEINASE INHIBITORS

CROSS REFERENCE TO RELATED APPLICATIONS

This application claims the benefit under 35 U.S.C. 119(e) of U.S. Provisional Application Serial No. 60/111,661, filed Dec. 10, 1998, hereby incorporated by reference in its entirety.

FIELD OF THE INVENTION

The present invention relates to compounds that inhibit procollagen C-proteinase, pharmaceutical compositions containing them, methods for their use, and methods for preparing these compounds.

BACKGROUND INFORMATION AND RELATED DISCLOSURES

The collagens are integral components of connective tissue. At present nineteen types of collagens have been identified. The interstitial collagen types I, II and III are the major collagen components of tissue. These collagens are synthesized as procollagen precusor molecules having amino- and carboxy-terminal peptide extensions also known as pro-regions. These pro-regions are typically cleaved upon secretion of the procollagen molecule to give a mature collagen molecule which is capable of association into highly structured collagen fibers. (see, e.g., Fessler and Fessler, *Annu. Rev. Biochem.* 47, 129, (1978); Kivirikko et al., *Extracellular Matrix Biochemistry* (1984) and Kuhn, *Structure and Function of Collagen Types* (eds Mayne, R and Burgeson, R. E.), Academic Press, Inc., Orlando, Fla. pp 1–42 (1987).

Excessive collagen deposition is associated with a variety of fibrotic diseases such as interstitial pulmonary fibrosis, pericentral fibrosis, Symmers' fibrosis, perimuscular fibrosis, kidney fibrosis, endocardial sclerosis, hepatitis, acute respiratory distress syndrome, arthritis, cystic fibrosis, surgical adhesions, tendon surgery, corneal scarring, scleroderma, chronic allograft rejection, hemodialysis shunt fibrosis and restenosis. These diseases are characterized by excessive deposits of fibrillar interstitial collagens that are resistant to proteolyic degradation thus leading to the symptoms of fibrosis. Therefore, inhibition of the pathological deposition of these collagens should help in the treatment of these diseases.

Recent studies suggest that procollagen C-proteinase is the essential enzyme that catalyzes the cleavage of the C-propeptide of types I, II and III collagens and therefore instrumental in the formation of functional collagen fibers ((see, Fertala et al., *J. Biol. Chem.*, 269, 11584, (1994)). It would therefore be desirable to provide procollagen C-proteinase inhibitors and thereby provide a means of combating diseases mediated by excessive deposition of these collagens. This invention fulfills this and related needs.

SUMMARY OF THE INVENTION

In a first aspect, this invention provides hydroxamic acids selected from the group of compounds represented by Formula (I):

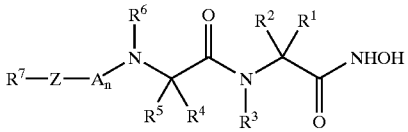

wherein:
$R^1$ and $R^4$ are, independently of each other, hydrogen or alkyl;

$R^2$ is:
(i) cycloalkyl, cycloalkylalkyl, aryl, aralkyl, aralkenyl, heteroaryl, heteroaralkyl, heteroaralkenyl, heterocyclo or heterocycloalkyl; or ii) -(alkylene)-$B^1$—X where $B^1$ is —O—, —$NR^8$—, —$S(O)_{0-2}$, —C=O, —$CONR^8$—, —$NR^8CO_2$—, $NR^8SO_2$— or —$C(=NR^8)NR^8SO_2$— (where $R^8$ is H or alkyl), and X is cycloalkyl, cycloalkylalkyl, aryl, aralkyl, heteroaryl, or heteroaralkyl; or (iii) -(alkylene)-$B^1$—X where $B^1$ is —$NR^8CO$— (where $R^8$ is H or alkyl), and X is cycloalkyl, cycloalkylalkyl, aryl, aralkyl, heteroaryl or heteroaralkyl; or (iv) $R^2$ and $R^3$ form an alkylene or heteroalkylene chain; with the proviso that $R^2$ does not contain an imidazole group.

$R^3$ is hydrogen or alkyl;

$R^6$ is hydrogen, alkyl, cycloalkyl, cycloalkylalkyl, aryl, aralkyl, heteroaryl or heteroaralkyl;

$R^5$ is:
(i) hydrogen, alkyl, cycloalkyl, cycloalkylalkyl, aryl, aralkyl, aralkenyl, heteroaryl, heteroaralkyl, heteroaralkenyl, heterocycloalkyl, heteroalkyl, or -(alkylene)-C(O)—X1 where $X^1$ is alkyl, hydroxy, alkoxy, aryl, aralkyl, aryloxy, aralkyloxy, heteroaryl, heteroaryloxy, heteroaralkyloxy or NR'R" (where R' and R" are independently H or alkyl, or R'and R" form an alkylene chain); or (ii) $R^5$ and $R^4$ form an alkylene chain; or (iii) $R^5$ and $R^6$ form an alkylene chain;

n is 0 or 1;

A is —$N(R^{10})$—$(CH_2)_m$—$CH(R^9)$—C(=O)— wherein:
m is an integer from 0–5 inclusive;
$R^9$ is hydrogen, alkyl, cycloalkyl, cycloalkylalkyl, aryl, aralkyl, heteroaryl, heteroaralkyl, heterocycloalkyl, heteroalkyl, or -(alkylene)-C(O)—$X^1$ where $X^1$ is alkyl, hydroxy, alkoxy, aryl, aralkyl, aryloxy, aralkyloxy, heteroaryl, heteroaryloxy, heteroaralkyloxy or NR'R" (where R' and R" are independently H or alkyl, or R' and R" form an alkylene chain); and
$R^{10}$ is hydrogen, alkyl, aralkyl or heteroaralkyl;

Z is Y—$B^2$ wherein:
Y is alkylene or a bond; and
$B^2$ is —CO—, —OC(O)—,
with the proviso that when $R^2$ is benzyl then Z is not —OC(O)—;

$R^7$ is cycloalkyl, cycloalkylalkyl, aryl, aralkyl, heteroaryl or heteroaralkyl;

or a pharmaceutically acceptable salt, prodrug, or isomer thereof.

In a second aspect, this invention provides a method of treatment of a disease in a mammal treatable by administration of a procollagen C-proteinase inhibitor selected from the group of compounds represented by Formula (I):

In a third aspect, this invention provides pharmaceutical compositions containing a therapeutically effective amount of a compound of Formula (I) or its pharmaceutically acceptable salt and a pharmaceutically acceptable excipient.

In a fourth aspect, this invention provides a method of treating disease by administering to a patient a selective inhibitor of procollagen-C-proteinase.

In a fifth aspect, this invention provides a method of preparing compounds of Formula (I).

DETAILED DESCRIPTION OF THE INVENTION

Definitions

Unless otherwise stated, the following terms used in the specification and claims have the meanings given below:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, pentyl, and the like.

"Alkylene" means a linear saturated divalent hydrocarbon radical of one to six carbon atoms or a branched saturated divalent hydrocarbon radical of three to six carbon atoms, e.g., methylene, ethylene, propylene, 2-methylpropylene, pentylene, and the like.

"Heteroalkylene" means an alkylene chain in which one methylene group has been replaced by O, S or NR' (where R' is hydrogen or alkyl.)

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkenylene" means a linear divalent hydrocarbon radical of two to six carbon atoms or a branched monovalent hydrocarbon radical of three to six carbon atoms, containing at least one double bond, e.g., ethenylene, 2-propenylene, and the like.

"Acyl" means a radical —C(O)R where R is hydrogen, alkyl, alkenyl, cycloalkyl, cycloalkylalkyl, haloalkyl, aryl, aralkyl, aralkenyl, heteroaryl, heteroaralkyl, heteroaralkenyl, or heterocyclo, e.g., acetyl, benzoyl, thenoyl, and the like.

"Acyloxy" means a radical —OC(O)R where R is hydrogen, alkyl, alkenyl, cycloalkyl, cycloalkylalkyl, aryl, aralkyl, aralkenyl, or haloalkyl, e.g., acetoxy, 3,3,3-trifluoroacetoxy and the like.

"Acylamino" means a radical —NRC(O)R' where R is hydrogen or alkyl and R' is hydrogen, alkyl, alkenyl, cycloalkyl, cycloalkylalkyl, heteroalkyl, haloalkyl, aryl, aralkyl, aralkenyl, heteroaryl, heteroaralkenyl, or heteroaralkyl, e.g., acetylamino, trifluoroacetylamino, benzoylamino, methylacetylamino, and the like.

"Sulfonylamino" means a radical —NRSO$_2$R' where R is hydrogen or alkyl and R' is alkyl, alkenyl, cycloalkyl, cycloalkylalkyl, heteroalkyl, haloalkyl, amino, monosubstituted amino, disubstituted amino, aryl, aralkyl, aralkenyl, heteroaryl, heteroaralkenyl, or heteroaralkyl, e.g., methylsulfonylamino, benzylsulfonylamino, N-methylaminosulfonylamino, and the like.

"Halo" means fluoro, chloro, bromo, or iodo, preferably fluoro and chloro.

"Haloalkyl" means alkyl substituted with one or more same or different halo atoms, e.g., $CH_2Cl$, —$CF_3$, —$CH_2CF_3$, —$CH_2CCl_3$, and the like.

"Cycloalkyl" means a saturated monovalent cyclic hydrocarbon radical of three to six ring carbons, e.g., cyclopropyl, cyclopentyl, cyclohexyl, and the like.

"Carbocycle" means a saturated, cyclic group of 3 to 8 ring atoms in which all the ring atoms are carbon, e.g., cyclopentyl, cyclohexyl, and the like.

"Aryl" means a monovalent monocyclic or bicyclic aromatic hydrocarbon radical of 6 to 10 ring atoms, optionally fused to a carbocycle or heterocycle, and optionally substituted independently with one or more substituents, preferably one or two substituents selected from alkyl, heteroalkyl, haloalkyl, halo, nitro, acyloxy, cyano, cycloalkyl, cycloalkylalkyl, optionally substituted phenyl, optionally substituted phenylalkyl, heteroaryl, heteroaralkyl, —OR (where R is hydrogen, alkyl, haloalkyl, alkenyl, cycloalkyl, cycloalkylalkyl, optionally substituted phenyl, heteroaryl, optionally substituted phenylalkyl, or heteroaralkyl), —NRR' (where R and R' are independently hydrogen, alkyl, alkenyl, haloalkyl, cycloalkyl, cycloalkylalkyl, optionally substituted phenyl, optionally substituted phenylalkyl, optionally substituted phenylalkenyl, heteroaryl, or heteroaralkyl), —C(O)R (where R is hydrogen, alkyl, alkenyl, cycloalkyl, cycloalkylalkyl, haloalkyl, optionally substituted phenyl, optionally substituted phenylalkyl, optionally substituted phenylalkenyl, heteroaryl, heteroaralkyl, or heteroaralkenyl), —S(O)$_n$R (where n is an integer from 0 to 2 and R is hydrogen (provided that n is 0), alkyl, haloalkyl, alkenyl, cycloalkyl, cycloalkylalkyl, optionally substituted phenyl, heteroaryl, optionally substituted phenylalkyl, or heteroaralkyl), —SO$_2$NRR' (where R and R' are independently hydrogen, alkyl, alkenyl, haloalkyl, cycloalkyl, cycloalkylalkyl, optionally substituted phenyl, optionally substituted phenylalkyl, optionally substituted phenylalkenyl, heteroaryl or heteroaralkyl, or R and R' together with the nitrogen they are attached to form a cycloamino ring), —COOH, -(alkylene)-COOH, -(alkenylene)-COOH, —COOR$^a$, -(alkenylene)-COOR$^a$, -(alkylene)-COOR$^a$ (where R$^a$ is alkyl, optionally substituted phenylalkyl, or heteroaralkyl), —CONR'R", -(alkylene)-CONR'R" (where R' and R" are independently selected from hydrogen, alkyl, cycloalkyl, cycloalkylalkyl, optionally substituted phenyl, optionally substituted phenylalkyl, heteroaryl and heteroaralkyl, or R' and R" together with the nitrogen they are attached to form a cycloamino ring), —NRC(O)R' (where R is hydrogen or alkyl and R' is hydrogen, alkyl, alkenyl, cycloalkyl, cycloalkylalkyl, haloalkyl, optionally substituted phenyl, optionally substituted phenylalkyl, optionally substituted phenylalkenyl, heteroaryl, heteroaralkenyl, or heteroaralkyl), —NRSO$_2$R' (where R is hydrogen or alkyl and R' is alkyl, alkenyl, cycloalkyl, cycloalkylalkyl, haloalkyl, optionally substituted phenyl, optionally substituted phenylalkyl, optionally substituted phenylalkenyl, heteroaryl, heteroaralkenyl, or heteroaralkyl), or —NRSO$_2$NR'R" (where R is hydrogen or alkyl and R' and R" are independently hydrogen, alkyl, alkenyl, haloalkyl, cycloalkyl, cycloalkylalkyl, optionally substituted phenyl, optionally substituted phenylalkyl or optionally substituted phenylalkenyl, or R' and R" together with the nitrogen they are attached to form a cycloamino ring). More specifically the term aryl includes, but is not limited to, phenyl, 1-naphthyl, 2-naphthyl, tetrahydronaphthyl, methylenedioxyphenyl, indanyl, tetralyl, indolinyl, chromanyl, isochromanyl and the like.

"Heteroaryl" means a monovalent monocyclic or bicyclic aromatic radical of 5 to 10 ring atoms containing one, two, or three ring heteroatoms selected from N, O, or S, the remaining ring atoms being C. The heteroaryl ring is optionally substituted independently with one or more substituents, preferably one or two substituents, selected from alkyl, haloalkyl, halo, nitro, cyano, cycloalkyl, cycloalkylalkyl, optionally substituted phenyl, optionally substituted phenylalkyl, —OR (where R is hydrogen, alkyl, haloalkyl, alkenyl, cycloalkyl, cycloalkylalkyl, optionally substituted phenyl or optionally substituted phenylalkyl), —NRR' (where R and R' are independently hydrogen, alkyl, alkenyl, haloalkyl, cycloalkyl, cycloalkylalkyl, optionally substituted phenyl, optionally substituted phenylalkyl or optionally substituted phenylalkenyl, or R and R" together with the nitrogen they are attached to form a cycloamino ring), —C(O)R (where R is hydrogen, alkyl, alkenyl, cycloalkyl, cycloalkylalkyl, haloalkyl, optionally substituted phenyl, optionally substituted phenylalkyl, or optionally substituted phenylalkenyl), —S(O)$_n$R (where n is an integer from 0 to 2 and R is hydrogen (provided that n is 0), alkyl, haloalkyl, alkenyl, cycloalkyl, cycloalkylalkyl, optionally substituted phenyl, or optionally substituted phenylalkyl), —SO$_2$NRR' (where R and R' are independently hydrogen, alkyl, alkenyl, haloalkyl, cycloalkyl, cycloalkylalkyl, optionally substituted phenyl, optionally substituted phenylalkyl or optionally substituted phenylalkenyl, or R and R" together with the nitrogen they are attached to form a cycloamino ring), —COOH, -(alkylene)-COOH, -(alkenylene)COOH, —COOR$^a$, -(alkenylene)-COOR$^a$, -(alkylene)-COOR$^a$ (where R$^a$ is alkyl, or optionally substituted phenylalkyl), —CONR'R", -(alkylene)-CONR'R", (where R' and R" are independently selected from hydrogen, alkyl, cycloalkyl, cycloalkylalkyl, optionally substituted phenyl and optionally substituted phenylalkyl, or R' and R" together with the nitrogen they are attached to form a cycloamino ring), —NRC(O)R' (where R is hydrogen or alkyl and R' is hydrogen, alkyl, alkenyl, cycloalkyl, cycloalkylalkyl, haloalkyl, optionally substituted phenyl, optionally substituted phenylalkyl, or optionally substituted phenylalkenyl), —NRSO$_2$R' (where R is hydrogen or alkyl and R' is alkyl, alkenyl, cycloalkyl, cycloalkylalkyl, haloalkyl, optionally substituted phenyl, optionally substituted phenylalkyl, or optionally substituted phenylalkenyl), —NRSO$_2$NR'R" (where R is hydrogen or alkyl and R' and R" are independently hydrogen, alkyl, alkenyl, haloalkyl, cycloalkyl, cycloalkylalkyl, optionally substituted phenyl, optionally substituted phenylalkyl or optionally substituted phenylalkenyl, or R' and R" together with the nitrogen they are attached to form a cycloamino ring), or an amino protecting group. More specifically the term heteroaryl includes, but is not limited to, furyl, thienyl, pyrroly, pyridyl, purinyl, pyrimidinyl, pyrazolyl, thiazolyl, imidazolyl, thiazolyl, thiadiazolyl, indolyl, azaindolyl, benzofuranyl, benzimidazolyl, benzthiazolyl, quinolinyl, isoquinolinyl, benzotriazolyl, benzopyranyl, 1, and the derivatives thereof.

"Optionally substituted phenyl" means phenyl ring which is optionally substituted with one or more substituents, preferably one or two substituents selected from alkyl, haloalkyl, halo, nitro, cyano, —NRR' (where R and R' are independently selected from hydrogen and alkyl, or R and R' together with the nitrogen they are attached to form a cycloamino ring), —OR (where R is hydrogen, alkyl or haloalkyl), —COOR$^a$ (where R$^a$ is hydrogen or alkyl) or —CONR'R" (where R' and R" are independently selected from hydrogen and alkyl, or R' and R" together with the nitrogen they are attached to form a cycloamino ring). Representative examples include, but are not limited to, 4-fluorophenyl, 3,4-dibromophenyl, 4-chloro-2,5-dimethylphenyl, 2,4,5-trichlorophenyl, 4-bromo-2-trifluoromethoxyphenyl, 2-chloro-4-trifluoromethyl, 4-tertbutylphenyl, 4-methoxyphenyl, 3-nitrophenyl, and the like.

"Heterocycle" or "Heterocyclo" means a saturated cyclic radical of 3 to 8 ring atoms in which one or two ring atoms are heteroatoms selected from N, O, or S(O)$_n$ (where n is an integer from 0 to 2), the remaining ring atoms being C, where one or two C atoms may optionally be replaced by a carbonyl group. The heterocyclo ring may be optionally substituted independently with one, two, or three substituents selected from alkyl, haloalkyl, cycloalkyl, cycloalkylalkyl, aryl, aralkyl, heteroaryl, heteroaralkyl, halo, cyano, acylamino, amino, monosubstituted amino, disubstituted amino, —OR (where R is hydrogen, alkyl, haloalkyl, alkenyl, cycloalkyl, cycloalkylalkyl, aryl, heteroaryl, aralkyl, or heteroaralkyl), —C(O)R (where R is hydrogen, alkyl, alkenyl, cycloalkyl, cycloalkylalkyl, haloalkyl, aryl, aralkyl, aralkenyl, heteroaryl, heteroaralkyl, or heteroaralkenyl), —S(O)$_n$R [where n is an integer from 0 to 2 and R is hydrogen (provided that n is 0), alkyl, haloalkyl, alkenyl, cycloalkyl, cycloalkylalkyl, amino, monosubstituted amino, disubstituted amino, aryl, heteroaryl, aralkyl, or heteroaralkyl], —COOH, -(alkylene)-COOH, —COOR$^a$, -(alkylene)-COOR$^a$ (where R$^a$ is alkyl, heteroalkyl, aralkyl, or heteroaralkyl), —CONR'R", -(alkylene)-CONR'R" (where R' and R" are independently selected from hydrogen, alkyl, cycloalkyl, cycloalkylalkyl, aryl, aralkyl, heteroaryl and heteroaralkyl, or R' and R" together with the nitrogen they are attached to form a cycloamino ring) or an amino protecting group. More specifically the term heterocyclo includes, but is not limited to, tetrahydropyranyl, piperidino, piperazino, morpholino and thiomorpholino, thiomorpholino-1-oxide, thiomorpholino-1,1-dioxide, and the derivatives thereof.

The term "cycloamino" means a heterocyclo group in which at least one ring atom is nitrogen. Specific examples include piperidine, piperazine, morpholine, thiamorpholine, thiamorpholine sulfoxide and thiamorpholinesulphone.

"Heteroalkyl" means an alkyl, cycloalkyl, or cycloalkylalkyl radical as defined above, carrying a substituent selected from —NR$^a$R$^b$, —OR$^c$, or —S(O)$_n$R$^d$, wherein:

n is an integer from 0 to 2,

R$^a$ is hydrogen, alkyl, haloalkyl, cycloalkyl, cycloalkylalkyl, aryl, aralkyl, aralkenyl, heteroaryl, heteroaralkyl, heteroaralkenyl, or acyl;

R$^b$ is hydrogen, alkyl, aryl, aralkyl, acyl, —SO$_2$R (where R is alkyl, haloalkyl, amino, monosubstituted amino or disubstituted amino), —COOR (where R is alkyl, aralkyl, or heteroaralkyl), —CONR'R", -(alkylene) CONR'R" (where R' and R" are independently selected from hydrogen, alkyl, cycloalkyl, cycloalkylalkyl, aryl, aralkyl, heteroaryl and heteroaralkyl, or R' and R" together with the nitrogen they are attached to form a cycloamino ring);

or R$^a$ and R$^b$ together with the nitrogen atom which they are attached to form a cycloamino ring.

R$^c$ is hydrogen, alkyl, haloalkyl, cycloalkyl, cycloalkylalkyl, aryl, aralkyl, aralkenyl, heteroaryl, heteroaralkyl, heteroaralkenyl, acyl, —CONR'R" (where R' and R" are independently selected from hydrogen, alkyl, cycloalkyl, cycloalkylalkyl, aryl, aralkyl, heteroaryl and heteroaralkyl, or R' and R" together with the nitrogen they are attached to form a cycloamino ring).

R$^d$ is hydrogen, alkyl, haloalkyl, cycloalkyl, cycloalkylalkyl, aryl, aralkyl, aralkenyl, heteroaryl, heteroaralkyl, heteroaralkenyl, acyl, -and additionally when n=0, CONR'R" (where R' and R" are independently selected from hydrogen, alkyl, cycloalkyl, cycloalkylalkyl, aryl, aralkyl, heteroaryl and heteroaralkyl, or R' and R" together with the nitrogen they are attached to form a cycloamino ring) and when n=2, NR'R" where R' and R" have the meanings given immediately above.

Representative examples of heteroalkyl include, but are not limited to 2-methoxyethyl, benzyloxymethyl, thiophen-2-ylthiomethyl, and the like;

"Cycloalkylalkyl" means a radical —$R^a R^b$ where R' is an alkylene group and $R^b$ is a cycloalkyl group as defined above e.g., cyclopropylmethyl, cyclohexylpropyl, 3-cyclohexyl-2-methylpropyl, and the like.

"Aralkyl" means a radical —$R^a R^b$ where $R^a$ is an alkylene group and $R^b$ is an aryl group as defined above e.g., benzyl, phenylethyl, 3-(3-chlorophenyl)-2-methylpentyl, and the like.

"Aralkenyl" means a radical —$R^a R^b$ where $R^a$ is an alkenyl group and $R^b$ is an aryl group as defined above e.g., 3-phenyl-2-propenyl, and the like.

"Heteroaralkyl" means a radical —$R^a R^b$ where $R^a$ is an alkylene group and $R^b$ is a heteroaryl group as defined above e.g., pyridin-3-ylmethyl, 3-(benzofuran-2-yl)propyl, and the like.

"Heteroaralkenyl" means a radical —$R^a R^b$ where $R^a$ is an alkenyl group and $R^b$ is a heteroaryl group as defined above e.g., 3-pyridin-3-ylpropen-2-yl, and the like.

"Heterocycloalkyl" means a radical —$R^a R^b$ where $R^a$ is an alkylene group and $R^b$ is a heterocyclo group as defined above e.g., tetrahydropyran-2-ylmethyl, 4-methylpiperazin-1-ylethyl, and the like.

"Alkoxy", "aryloxy", "heteroaryloxy", "aralkyloxy", or "heteroaralkyloxy" means a radical —OR where R is an alkyl, aryl, heteroaryl, aralkyl, or heteroaralkyl respectively, as defined above e.g., methoxy, phenoxy, pyridin-2-yloxy, benzyloxy, and the like.

"Optional" or "optionally" means that the subsequently described event or circumstance may but need not occur, and that the description includes instances where the event or circumstance occurs and instances in which it does not. For example, "heterocyclo group optionally mono- or di- substituted with an alkyl group" means that the alkyl may but need not be present, and the description includes situations where the heterocyclo group is mono- or disubstituted with an alkyl group and situations where the heterocyclo group is not substituted with the alkyl group.

The term "protecting group" refers to a grouping of atoms that when attached to a reactive group in a molecule masks, reduces or prevents that reactivity. Examples of protecting groups can be found in T. W. Greene and P. G. Futs, *Protective Groups in Organic Chemistry*, (Wiley, 2nd ed. 1991) and Harrison and Harrison et al., *Compendium of Synthetic Organic Methods*, Vols. 1–8 (John Wiley and Sons. 1971–1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like. Representative hydroxy protecting groups include those where the hydroxy group is either acylated or alkylated such as benzyl and trityl ethers as well as alkyl ethers, tetrahydropyranyl ethers, trialkylsilyl ethers and allyl ethers.

The term "protected hydroxylamine derivative" refers to a modified hydroxylamine whose nitrogen and/or hydroxyl groups are protected such that the nitrogen atom may be selectively monoacylated.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. For example, if the $R^1$ and $R^2$ substituents in a compound of formula (I) are different, then the carbon to which they are attached is an asymmetric center and therefore the compound of formula (I) can exist as an (R)- or (S)-stereoisomer. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-napthalenesulfonic acid, 4-toluenesulfonic acid, camphorsulfonic acid, 4-methylbicyclo[2.2.2]-oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Pro-drugs" means any compound which releases an active parent drug according to Formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs include compounds of Formula (I) wherein a hydroxy, amino, or sulfhydryl group in a compound of Formula (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of Formula (I), and the like.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Nomenclature

Compounds of this invention may be conveniently named with reference to their amino acid components in accordance with nomenclature conventional to the peptide field.

For example a dipeptide where n is 0, $R^1=R^3=R^4=R^6=H$, $R^2$ is 4-thiazolylmethyl, $R^5$ is (S,S)-1-methylpropyl and $ZR^7$ is benzyloxycarbonyl, is named as CBz-Ile-4-Taz-NHOH. With respect to the synthetic schemes A and B subsequently presented, 4-Taz (4-thiazolylalanine) represents $AA_1$ and Ile represents $AA_2$.

A tripeptide where n is 1 and m is 0, $R^1=R^3=R^4=R^6=R^9=$ H, $R^2$ is 4-thiazolylmethyl, $R^5$ is (S,S)-1-methylpropyl, $ZR^7$ is 4-chlorobenzoyl and $R^{10}$ is 4-fluorobenzyl is named 4-chlorobenzoyl-(4-fluorobenzyl)Gly-Ile-Taz-NHOH. With respect to the synthetic schemes A and B subsequently presented, 4-Taz represents $AA_1$, Ile represents $AA_2$ and (4-fluorobenzyl)Gly represents $AA_3$.

Preferred Embodiments

While the broadest definition of this invention is set forth in the Summary of the Invention, certain compounds of formula (I) are preferred.

One class of compounds are the dipeptidic hydroxamic acids corresponding to compounds of Formula 1 where n is 0. Another class of compounds are the tripeptidic hydroxamic acids corresponding to compounds of Formula 1 where n is 1. For both the dipeptidic and tripeptidic hydroxamic acid compounds of the invention, particularly preferred are those where $R^2$ is heteroaralkyl, particularly 4-thiazolylmethyl and $R^5$ is (S,S)-1-methylpropyl. Preferably, $R^2$, $R^5$ and $R^9$ are present in the naturally ocurring amino acid configuration, i.e. derived from the (L) amino acids.

Another class of preferred compounds of Formula I is that where Z is C(O)O. Another class of preferred compounds of Formula I is that where Z is $S(O)_2$. Within each of these classes of compounds, more preferred are those where $R^7$ is aryl, aralkyl or heteroaryl, particularly halophenyl (e.g. 3,4-dibromophenyl, 2,5-dichlorophenyl or 2,4,5-trichlorophenyl), benzyl (optionally substituted) (e.g. benzyl or 3,4-dichlorobenzyl) or halothienyl (e.g. 4,5-dibromothien-2-yl). When Z is C=O, also preferred are $R^7$ being aralkyl or heteroaralkyl, particularly benzyl or heteroarylmethyl substituted with halo, preferably one or two chloro.

Another class of preferred compounds is that where $R^2$ is aralkyl or heteroaralkyl. Within this class, more preferred are those compounds where $R^2$ is 3-indolyl methyl, 2-thienylmethyl, 4-imidazolylmethyl or 4-thiazolylmethyl, particularly 4-thiazolylmethyl.

Another class of preferred compounds are those where $R^2$ is (alkylene)-B—X where B is —O—, —$NR^8$—, —S—, —C=O, —$CONR^8$—, —$NR^8CO_2$—, —$NR^8SO_2$— or —C(=$NR^8$)$NR^8SO_2SO$—-(where $R^8$ is independently H or alkyl), and X is cycloalkyl, cycloalkylalkyl, aryl, aralkyl heteroaryl or heteroaralkyl. Particularly preferred are compounds where the alkylene group is methylene, B is —$NR^8CO_2$ and X is aralkyl.

A fourth class of preferred compounds are those where $R^5$ is alkyl or phenyl, particularly propyl, 1-methylethyl, or (S,S)-1-methylpropyl. Within this class of compounds, particularly preferred are those where $R^1$ and $R^4$ are hydrogen and $R^2$ is heteroaralkyl, particularly 4-thiazolylmethyl.

Representative Compounds of This Invention that Have Been Prepared According to the Schemes and Examples are as Follows I. Dipeptidic hydroxamic acids of Formula (I) where n=0, $R^1=R^3=R^4=R^6$=hydrogen and $ZR^7$ is benzyloxycarbonyl and other groups are as defined below are:

TABLE I

| Compound | Example | St* | R2 | St** | R5 | m/e |
|---|---|---|---|---|---|---|
| 1 | I | S | 4-thiazolylmethyl | S | phenyl | 455 |
| 2 | I | S | 4-thiazolylmethyl | S | 2-carboxyethyl | 451 |
| 3 | I | S | 4-thiazolylmethyl | S | isobutyl | 435 |
| 4 | I | S | 4-thiazolylmethyl | S | n-butyl | 435 |
| 5 | I | S | 4-thiazolylmethyl | S | ethyl | 407 |
| 6 | I | S | 4-thiazolylmethyl | S | 2-phenethyl | 483 |
| 7 | I | S | 4-thiazolylmethyl | S | 3-indolylmethyl | 508 |

TABLE I-continued

| Compound | Example | St* | R2 | St** | R5 | m/e |
|---|---|---|---|---|---|---|
| 8 | I | S | 4-thiazolylmethyl | S | hydroxymethyl | 409 |
| 9 | I | S | 4-thiazolylmethyl | S,R | 1-benzyloxyethyl | 513 |
| 10 | I | S | 4-thiazolylmethyl | S | 4-fluorobenzyl | 487 |
| 11 | I | S | 4-thiazolylmethyl | S | benzyl | 469 |
| 12 | I | S | 4-thiazolylmethyl | S | methyl | 393 |
| 13 | I | S | 4-thiazolylmethyl | S | 1-naphthylmethyl | 519 |
| 14 | I | S | (E)-styrylmethyl | S,S | 1-methylpropyl | 454 |
| 15 | I | S | 2-bromobenzyl | S,S | 1-methylpropyl | 506 |
| 16 | I | S | 3-thienylmethyl | S,S | 1-methylpropyl | 434 |
| 17 | I | S | 5-(2-bromothienyl)methyl | S,S | 1-methylpropyl | 511 |
| 18 | I | S | 2-furylmethyl | S,S | 1-methylpropyl | 418 |
| 19 | I | S | 3-benzothienylmethyl | S,S | 1-methylpropyl | 484 |
| 20 | I | S | 4-fluorobenzyl | S,S | 1-methylpropyl | 446 |
| 21 | I | S | benzyloxymethyl | S,S | 1-methylpropyl | 458 |
| 22 | I | S,R | 1-benzyloxyethyl | S,S | 1-methylpropyl | 472 |
| 23 | I | S | 3-chlorobenzyl | S,S | 1-methylpropyl | 462 |
| 24 | I | S | 4-thiazolylmethyl | S | cyclopropylmethyl | 433 |
| 25 | I | S | 4-thiazolylmethyl | S | cyclohexyl | 461 |
| 26 | I | S | 4-thiazolylmethyl | S | 2-methylthioethyl | 453 |
| 27 | I | S | 4-thiazolylmethyl | S | carbamoylmethyl | 436 |
| 28 | I | R | 3-indolylmethyl | S | 2-methylthioethyl | 485 |
| 29 | I | R | 3-indolylmethyl | S | butyl | 467 |
| 30 | I | R | 3-indolylmethyl | S | phenyl | 487 |
| 31 | I | S | 3-indolylmethyl | S,S | 1-methylpropyl | 466 |
| 32 | I | S | 3-indolylmethyl | S | 1-naphthylmethyl | 551 |
| 33 | I | S | 3-indolylmethyl | R | 2-naphthylmethyl | 551 |
| 34 | I | S | 3-indolylmethyl | R | 2-naphthylmethyl | 551 |
| 35 | I | S | 3-indolylmethyl | S | 2-naphthylmethyl | 551 |
| 36 | I | S | 3-indolylmethyl | S | 2-phenethyl | 515 |
| 37 | I | S | 3-indolylmethyl | S | 4-fluorobenzyl | 519 |
| 38 | I | S | 3-indolylmethyl | S | ethyl | 439 |
| 39 | I | S | 3-indolylmethyl | S | isopropyl | 453 |
| 40 | I | S | 3-indolylmethyl | R | 2-carboxyethyl | 483 |
| 41 | I | R | 3-indolylmethyl | R | 2-(N-hydroxycarbamoyl)ethyl | 498 |
| 42 | I | S | (1-benzyl-1H-imidazol-4-yl)methyl | S,S | 1-methylpropyl | 508 |
| 43 | I | S | 4-(2,6-dichlorobenzyloxy)benzyl | S,S | 1-methylpropyl | 602 |
| 44 | I | S | 2-cyclohexyloxycarbonylethyl | S,S | 1-methylpropyl | 492 |
| 45 | I | S | 2-phenethyl | S,S | 1-methylpropyl | 442 |
| 46 | I | S | 4-methylbenzylthiomethyl | S,S | 1-methylpropyl | 488 |
| 47 | I | S | 2-naphthylmethyl | S,S | 1-methylpropyl | 478 |
| 48 | I | S | 4-benzyloxycarbonylaminobutyl | S,S | 1-methylpropyl | 543 |
| 49 | I | S | 4-methoxybenzyl | S,S | 1-methylpropyl | 458 |
| 50 | I | S | 4-benzyloxybenzyl | S,S | 1-methylpropyl | 534 |
| 51 | I | S | 4-methoxybenzylthiomethyl | S,S | 1-methylpropyl | 504 |
| 52 | I | S | 2-(4-methylbenzyl)thioethyl" | S,S | 1-methylpropyl | 502 |
| 53 | I | R | 4-fluorobenzyl | S,S | 1-methylpropyl | 446 |
| 54 | I | R | (1-benzyl-1H-imidazol-4-yl)methyl | S,S | 1-methylpropyl | 509 |
| 55 | I | S | 4-(2-chlorobenzylcarboxamido)butyl | S,S | 1-methylpropyl | 577 |
| 56 | I | S | (3-benzyloxymethyl-3H-imidazol-4-yl)methyl | S,S | 1-methylpropyl | 539 |
| 57 | I | S | (1H-imidazol-4-yl)methyl | S,S | 1-methylpropyl | 419 |
| 58 | I | S | 2-pyridylmethyl | S,S | 1-methylpropyl | 429 |
| 59 | I | S | 3-chlorobenzyl | S,S | 1-methylpropyl | 462 |
| 60 | I | S | 3,4-dichlorobenzyl | S,S | 1-methylpropyl | 496 |
| 61 | I | S | 4-nitrobenzyl | S,S | 1-methylpropyl | 473 |
| 62 | I | S | 4-bromobenzyl | S,S | 1-methylpropyl | 506 |

TABLE I-continued

| Compound | Example | St* | R2 | St** | R5 | m/e |
|---|---|---|---|---|---|---|
| 63 | I | S | 3-trifluoromethylbenzyl | S,S | 1-methylpropyl | 496 |
| 64 | I | S | 4-phenylbenzyl | S,S | 1-methylpropyl | 504 |
| 65 | I | S | indan-2-yl | S,S | 1-methylpropyl | 454 |
| 66 | I | S | benzyloxycarbonyl aminomethyl | S,S | 1-methylpropyl | 501 |
| 67 | I | S | 4-(4-tolylsulfonamido) butyl | S,S | 1-methylpropyl | 563 |
| 68 | I | S | 2-(4-nitrophenyl)ethyl | S,S | 1-methylpropyl | 499 |
| 69 | I | S | 3-(4-tosylguanidino)propyl | S,S | 1-methylpropyl | 591 |
| 70 | I | S | 4-tertbutylthiobenzyl | S,S | 1-methylpropyl | 516 |
| 71 | I | S | 3-tertbutoxybenzyl | S,S | 1-methylpropyl | 500 |
| 72 | I | S | 4-tertbutoxycarbonyl methylbenzyl | S,S | 1-methylpropyl | 558 |
| 73 | I | S | 4-carbamoylbenzyl | S,S | 1-methylpropyl | 471 |
| 74 | I | S | 4-acetamidobenzyl | S,S | 1-methylpropyl | 485 |
| 75 | I | S | 2-propargyl | S,S | 1-methylpropyl | 376 |
| 76 | I | S | 2-allyl | S,S | 1-methylpropyl | 378 |
| 77 | I | S | 4-thiazolylmethyl | S,S | 1-methylpropyl | 435 |

St* Stereochemistry at carbon attached to $R^2$ and of $R^2$ substituent (if it has an independent chiral centre)
St** Stereochemistry at carbon attached to $R^5$ and of $R^5$ substituent (if it has an independent chiral centre)

II. dipeptidic hydroxamic acids of Formula (I) where n=0, $R^1=R^3=R^4=R^6$=hydrogen and $R^4$ is (S,S)-1-methylpropyl and other groups are as defined below are:

TABLE II

| Compound | Example | St* | R2 | ZR7 | m/e |
|---|---|---|---|---|---|
| 1 | II | S | 4-thiazolylmethyl | 4-methoxybenzenesulfonyl | 471 |
| 2 | II | S | 4-thiazolylmethyl | benzenesulfonyl | 441 |
| 3 | II | S | 4-thiazolylmethyl | 2-chlorobenzenesulfonyl | 474 |
| 4 | II | S | 4-thiazolylmethyl | 3-chlorobenzenesulfonyl | 474 |
| 5 | II | S | 4-thiazolylmethyl | 4-chlorobenzenesulfonyl | 474 |
| 6 | II | S | 4-thiazolylmethyl | 2,4-dichlorobenzenesulfonyl | 508 |
| 7 | II | S | 4-thiazolylmethyl | 4-fluorobenzenesulfonyl | 458 |
| 8 | II | S | 4-thiazolylmethyl | 3-nitrobenzenesulfonyl | 485 |
| 9 | II | S | 4-thiazolylmethyl | 4-methylbenzenesulfonyl | 454 |
| 10 | II | S | 4-thiazolylmethyl | 3-trifluoromethylbenzenesulfonyl | 508 |
| 11 | II | S | 4-thiazolylmethyl | 4-bromo-2,5-difluorobenzenesulfonyl | 556 |
| 12 | II | S | 4-thiazolylmethyl | 5-dimethylamino-1-naphthalenesulfonyl | 533 |
| 13 | II | S | 4-thiazolylmethyl | 4-isopropylbenzenesulfonyl | 483 |
| 14 | II | S | 4-thiazolylmethyl | 2,4,6-trimethylbenzenesulfonyl | 483 |
| 15 | II | S | 4-thiazolylmethyl | 4-methoxy-2,3,6-trimethylbenzenesulfonyl | 512 |
| 16 | II | S | 4-thiazolylmethyl | 2,3,4,5,6-pentamethylbenzenesulfonyl | 511 |
| 17 | II | S | 4-thiazolylmethyl | 4,5-dibromothiophene-2-sulfonyl | 604 |
| 18 | II | S | 4-thiazolylmethyl | 3,4-dibromobenzenesulfonyl | 599 |
| 19 | II | S | 4-thiazolylmethyl | 4-chloro-2,5-dimethylbenzenesulfonyl | 503 |
| 20 | II | S | 4-thiazolylmethyl | 2,4,5-trichlorobenzenesulfonyl | 542 |
| 21 | II | S | 4-thiazolylmethyl | 4-bromo-2-(trifluoromethoxy)benzene sulfonyl | 604 |
| 22 | II | S | 4-thiazolylmethyl | 4-methoxynaphthalene-1-sulfonyl | 521 |
| 23 | II | S | 4-thiazolylmethyl | 4-benzenesulfonylthiophene-2-sulfonyl | 586 |
| 24 | II | S | 4-thiazolylmethyl | 2-chloro-4-(trifluoromethyl)benzenesulfonyl | 543 |
| 25 | II | S | 4-thiazolylmethyl | 5-chloronaphthalene-1-sulfonyl | 525 |

TABLE II-continued

| Compound | Example | St* | R2 | ZR7 | m/e |
|---|---|---|---|---|---|
| 26 | II | S | 4-thiazolylmethyl | 2,2,5,7,8-pentamethylchroman-6-sulfonyl | 567 |
| 27 | II | S | 4-thiazolylmethyl | 4-methoxy-2-nitrobenzenesulfonyl | 516 |
| 28 | II | S | 4-thiazolylmethyl | 1-naphthalenesulfonyl | 491 |
| 29 | II | S | 4-thiazolylmethyl | 5-methoxybenzofuran-2-sulfonyl) | 511 |
| 30 | II | S | 4-thiazolylmethyl | 4-tert-amylbenzenesulfonyl | 511 |
| 31 | II | S | 4-thiazolylmethyl | 4-(4-chlorophenoxy)benzenesulfonyl | 566 |
| 32 | II | S | 4-thiazolylmethyl | 2-(pyrid-2-yl)thiophene-5-sulfonyl | 523 |
| 33 | II | S | 4-thiazolylmethyl | 2-{3-[1-methyl-5-(trifluoromethyl)pyrazolyl]}thiophene-5-sulfonyl | 594 |
| 34 | II | S | 4-thiazolylmethyl | 3,5-dimethylisoxazole-4-sulfonyl | 460 |
| 35 | II | S | 4-thiazolylmethyl | benzofurazan-4-sulfonyl | 482 |
| 36 | III | S | 3-indolylmethyl | benzylcarbamoyl | 466 |
| 37 | IV | S | 3-indolylmethyl | phenylcarbamoyl | 452 |
| 38 | III | S | 3-indolylmethyl | benzoyl | 437 |
| 39 | IV | S | 3-indolylmethyl | 2-fluorophenylcarbamoyl | 470 |
| 40 | III | S | 3-indolylmethyl | 2-methoxyphenylcarbamoyl | 482 |
| 41 | III | S | 3-indolylmethyl | cyclohexylcarbamoyl | 458 |
| 42 | III | S | 3-indolylmethyl | 2-phenethylcarbamoyl | 480 |
| 43 | III | S | 3-indolylmethyl | 3,5-dichlorophenylcarbamoyl | 520 |
| 44 | IV | S | 3-indolylmethyl | 2,4-dichlorobenzoyl | 505 |
| 45 | IV | S | 3-indolylmethyl | 4-trifluoromethylbenzoyl | 505 |
| 46 | IV | S | 3-indolylmethyl | 3-methylbenzoyl | 451 |
| 47 | IV | S | 3-indolylmethyl | cyclohexanoyl | 443 |
| 48 | IV | S | 4-thiazolylmethyl | 3-furanoyl | 395 |
| 49 | IV | S | 4-thiazolylmethyl | cyclopentanoyl | 397 |
| 50 | IV | S | 4-thiazolylmethyl | 4-aminobenzoyl | 420 |
| 51 | IV | S | 4-thiazolylmethyl | 4-hydroxybenzoyl | 420 |
| 52 | IV | S | 4-thiazolylmethyl | 4-dimethylaminobenzoyl | 448 |
| 53 | V | S | 4-thiazolylmethyl | 3,4-dichlorobenzyloxycarbonyl | 503 |
| 54 | V | S | 4-thiazolylmethyl | 3-chlorobenzyloxycarbonyl | 468 |
| 55 | V | S | 4-thiazolylmethyl | 3-nitrobenzyloxycarbonyl | 480 |
| 56 | II | S | 4-thiazolylmethyl | 2-(1-naphthylethane)sulfonyl | 519 |
| 57 | IV | S | 4-thiazolylmethyl | (R/S)-2-(4-chlorophenoxy)propionyl | 483 |
| 58 | II | S | 4-thiazolylmethyl | 2-phenylbenzimidazole-5-sulfonyl | 557 |
| 59 | IV | S | 4-thiazolylmethyl | 3-isoquinolinecarbonyl | 456 |
| 60 | IV | S | 4-thiazolylmethyl | (P/Σ)-α-hydroxy-3-nitrophenylacetyl | 481 |
| 61 | X | S | 4-thiazolylmethyl | 1-carbonylmethyl-2,3,4,6,7,8,9,10-octahydro-1H-pyrimidino[1,2-a]azepin-5-ylium bromide | 494 |
| 62 | IV | S | 4-thiazolylmethyl | 4-fluorophenoxyacetyl | 452 |
| 63 | II | S | 4-thiazolylmethyl | 4-phenylazobenzenesulfonyl | 545 |
| 64 | VII | S | 4-thiazolylmethyl | 2-(4-chlorophenyl)ethylcarbamoyl | 482 |
| 65 | VII | S | 4-thiazolylmethyl | 3-phenylpropylcarbamoyl | 462 |
| 66 | X | S | 4-thiazolylmethyl | 1-(4-(2-nitrophenyl)piperazino)methylcarbonyl | 548 |
| 67 | IX | S | 4-thiazolylmethyl | 2-(3-chlorophenylsulfonamido)ethylcarbonyl | 546 |
| 68 | IV | S | 4-thiazolylmethyl | 4-vinylbenzoyl | 431 |
| 69 | IV | S | 4-thiazolylmethyl | 2-ethylsulfanylnicotinoyl | 466 |
| 70 | IV | S | 4-thiazolylmethyl | (R/S)-2-hydroxy-3-phenylpropionyl | 449 |
| 71 | IV | S | 4-thiazolylmethyl | 1-hydroxycyclopropylcarbonyl | 385 |
| 72 | IV | S | 4-thiazolylmethyl | (R/S)-tetrahydrofuran-3-carbonyl | 399 |
| 73 | IV | S | 4-thiazolylmethyl | (R)-(−)-2-oxo-4-thiazolidinecarbonyl | 430 |
| 74 | IV | S | 4-thiazolylmethyl | (S)-2-hydroxy-2-(1H- | 439 |

TABLE II-continued

| Compound | Example | St* | R2 | ZR7 | m/e |
|---|---|---|---|---|---|
| | | | | imidazol-4-yl)propionyl | |
| 75 | IV | S | 4-thiazolylmethyl | 5-chloro-2-thiophenecarbonyl | 444 |
| 76 | IV | S | 4-thiazolylmethyl | (R/S)-1-hydroxy-(4-methoxyphenyl)acetyl | 465 |
| 77 | IV | S | 4-thiazolylmethyl | (2,6-dihydroxypyrimidin-4-yl)acetyl | 453 |
| 78 | III | S | 4-thiazolylmethyl | cyclohexylcarbamoyl | 426 |
| 79 | I | S | benzyloxycarbonylaminomethyl | benzyloxycarbonyl | 501 |
| 80 | II | S | benzyloxycarbonylaminomethyl | 2,5-dichlorobenzenesulfonyl | 575 |
| 81 | II | S | benzyloxycarbonylaminomethyl | 3,4-dibromobenzenesulfonyl | 664 |
| 82 | II | S | benzyloxycarbonylaminomethyl | 4,5-dibromothiophene-2-sulfonyl | 670 |
| 83 | II | S | benzyloxycarbonylaminomethyl | 2,5-dimethyl-4-chlorobenzenesulfonyl | 569 |
| 84 | II | S | benzoylaminomethyl | benzyloxycarbonyl | 471 |
| 85 | II | S | 4-thiazolylmethyl | 2,5-dichlorobenzenesulfonyl | 508 |

St* Stereochemistry at carbon attached to $R^2$

III. Dipeptidic hydroxamic acids of Formula (I) where n=0, $R^1=R^3=R^6$=hydrogen and $ZR^7$ is benzyloxycarbonyl and other groups are as defined below are:

TABLE III

| Compound | Example | St* | R2 | R4 & R5 | |
|---|---|---|---|---|---|
| 1 | I | S | 3-indolylmethyl | propylene | 451 |
| 2 | I | S | 3-indolylmethyl | pentylene | 479 |
| 3 | I | S | 3-indolylmethyl | dimethyl | 439 |

St* - Stereochemistry at carbon attached to $R^2$

IV. Dipeptidic hydroxamic acids of Formula (I) where n=0, $R^1=R^3=R^4$=hydrogen, $R^2$ is (S) 3-indolymethyl and $ZR^7$ is benzyloxycarbonyl and other groups are as defined below are:

TABLE IV

| Compound | Example | St* | R5 | R6 | m/e |
|---|---|---|---|---|---|
| 1 | I | | H | methyl | 425 |
| 2 | I | S | 2-carboxyethyl | methyl | 497 |
| 3 | I | S | methyl | methy | 439 |
| 4 | I | S | isopropyl | methyl | 467 |
| 5 | I | S | benzyl | methyl | 515 |
| 6 | VI | | H | 2-methylpropyl | 467 |
| 7 | VI | | H | 4-pyridylmethyl | 502 |

St* - Stereochemistry at carbon attached to $R^5$

V. Tripeptidic hydroxamic acids of Formula I where n=1, m=0, $R^1=R^3=R^4=R^6$=H, $R^2$ is (S) 4-thiazolylmethyl, $R^5$ is (S,S)-1-methylpropyl and other groups are as defined below are:

TABLE V

| Compound | Example | St* | R9 | ZR7 | R10 | m/e |
|---|---|---|---|---|---|---|
| 1 | VIII | S | 2-methylthioethyl | benzyloxycarbonyl | H | 566 |
| 2 | VIII | S | 2-benzyloxycarbonylethyl | benzyloxycarbonyl | H | 654 |
| 3 | VIII | S | 3-indolylmethyl | benzyloxycarbonyl | H | 621 |
| 4 | VIII | S | 2-benzyloxycarbonylethyl | benzyloxycarbonyl | H | 654 |
| 5 | VIII | S | 4-fluorobenzyl | benzyloxycarbonyl | H | 600 |
| 6 | VIII | S | benzyloxymethyl | benzyloxycarbonyl | H | 612 |
| 7 | VIII | S | 2-methylpropyl | benzyloxycarbonyl | H | 548 |
| 8 | VIII | S | 4-hydroxybenzyl | benzyloxycarbonyl | H | 598 |
| 9 | VIII | S | benzyl | benzyloxycarbonyl | H | 582 |
| 10 | IX | S | benzyl | 2-chlorobenzyloxycarbonyl | H | 616 |
| 11 | VIII | S | 1-naphthylmethyl | benzyloxycarbonyl | H | 632 |
| 12 | VIII | S | phenyl | benzyloxycarbonyl | H | 568 |
| 13 | VIII | S | tert-butoxycarbonylmethyl | benzyloxycarbonyl | H | 606 |
| 14 | VIII | S,S | 1-methylpropyl | benzyloxycarbonyl | H | 548 |
| 15 | VIII | S | benzyl | benzyloxycarbonyl | methyl | 596 |
| 16 | X | | H | 4-chlorobenzoyl | 4-fluorobenzyl | 604 |
| 17 | X | | H | 3-chlorobenzoyl | 4-fluorobenzyl | 604 |
| 18 | X | | H | 3-methylbenzoyl | 4-fluorobenzyl | 584 |
| 19 | X | | H | phenylcarbamoyl | 4-fluorobenzyl | 585 |
| 20 | IX | S | benzyl | phenylcarbamoyl | H | 567 |
| 21 | X | | H | 4-nitrobenzoyl | 4-fluorobenzyl | 615 |

TABLE V-continued

| Compound | Example | St* | R9 | ZR7 | R10 | m/e |
|---|---|---|---|---|---|---|
| 22 | X | | H | 4-trifluoromethylbenzoyl | 4-fluorobenzyl | 638 |
| 23 | X | | H | 2-methoxybenzoyl | 4-fluorobenzyl | 600 |
| 24 | X | | H | 4-(N-hydroxycarbamimidoyl)benzoyl | 4-fluorobenzyl | 628 |
| 25 | X | | H | (R/S) 2-(4-chlorophenyl)-1-hydroxymethylethyl | H | 525 |
| 26 | X | | H | furfuryl | H | 438 |
| 27 | X | | H | 2-(4-morpholino)ethyl | H | 471 |
| 28 | X | | H | 2-pyridylmethyl | H | 449 |
| 29 | X | | H | 3-(1-imidazolyl)propyl | H | 466 |
| 30 | X | | H | 2,3-dimethoxybenzyl | H | 508 |
| 31 | X | | H | 3-nitrobenzyl | H | 493 |
| 32 | X | | H | 2-(4-chlorophenethyl) | H | 496 |
| 33 | IX | S | 4-fluorobenzyl | 4-tertbutylbenzenesulfonyl | H | 662 |
| 34 | IX | S | 4-fluorobenzyl | 3-chlorobenzenesulfonyl | H | 640 |
| 35 | IX | S | 4-fluorobenzyl | 2,4-dichlorobenzenesulfonyl | H | 674 |
| 36 | IX | S | 4-fluorobenzyl | 4-methoxybenzenesulfonyl | H | 636 |
| 37 | IX | S | 4-fluorobenzyl | 4-methylbenzenesulfonyl | H | 620 |
| 38 | IX | S | benzyl | 3-chlorobenzenesulfonyl | H | 622 |
| 39 | X | | H | 2,3-dichlorobenzenesulfonyl | 4-fluorobenzyl | 674 |
| 40 | X | | H | 4-tertbutylbenzenesulfonyl | 4-fluorobenzyl | 662 |

St* Stereochemistry at carbon attached to $R^9$ and of $R^9$ substituent (if it has an independent chiral centre)

VI. Miscellaneous tripeptidic hydroxamic acid compounds of the invention where n=1, m=1, $R^1=R^3=R^4R^6=H$, $R^2$ is (S)-4-thiazolylmethyl and $R^5$ is (S,S)-1-methylpropyl, and other groups are as defined below are include:

TABLE VI

| Compound | Example | R9 | ZR7 | R10 | m/e |
|---|---|---|---|---|---|
| 1 | IX | H | 3-bromobenzene-sulfonyl | H | 591 |
| 2 | IX | H | 3-nitrobenzene-sulfonyl | H | 557 |

Other miscellaneous compounds with $R^2$ and $R^3$ forming an alkylene or heteroalkylene chain include CBz-Ile-Pro-NHOH (m/e=378) and CBz-Ile-Thz-NHOH (m/e=396). Thz is thiazolidine-4-carboxylic acid.

Other miscellaneous compounds with $R^5$ and $R^6$ forming an alkylene chain include CBz-Pro-Trp-NHOH (m/e=451).

General Synthetic Scheme

Compounds of this invention may be made by several synthetic methods as described below.

The starting materials and reagents used in preparing these compounds are either available from commercial suppliers such as Aldrich Chemical Co., (Milwaukee, Wis., USA), Bachem (Torrance, Calif., USA), Emka-Chemie, or Sigma (St. Louis, Mo., USA) or are prepared by methods known to those skilled in the art following procedures set forth in references such as *Fieser and Fieser's Reagents for Organic Synthesis,* Volumes 1–15 (John Wiley and Sons, 1991); *Rodd's Chemistry of Carbon Compounds,* Volumes 1–5 and Supplementals (Elsevier Science Publishers, 1989), *Organic Reactions,* Volumes 1–40 (John Wiley and Sons, 1991), *March's* Advanced Organic Chemistry, (John Wiley and Sons, 4th Edition), and *Larock's* Comprehensive Organic Transformations (VCH Publishers Inc., 1989). In particular, a variety of natural and unnatural amino acids in various protected forms are available from specialty chemical suppliers such as Novabiochem Inc. (La Jolla, Calif.), Advanced Chemtech Inc. (Louisville, Ky.), Synthetech Inc. (Albany, Oreg.), Bachem Inc. (Torrance, Calif.). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like.

The compounds of the invention are C-terminal hydroxamic derivatives of natural and unnatural di- and tripeptides further functionalized at the N-terminus. They may be made by initially assembling the peptide precursor followed by deprotection (as necessary) and functionalization of the C- and N-termini. The peptide precursors are made by methods known to those of skill in the art of peptide synthesis, including solution phase chemistries and solid phase synthesis, see *Solid Phase Peptide Synthesis: A Practical*

*Approach* by E. Atherton and R. C. Sheppard (Oxford University Press, 1989)

In general, as shown in Schemes A and B, a C-terminal protected amino acid $P_1$-$AA_1$ is coupled to an N-protected amino acid $AA_2$-$P_2$ to give a compound $P_1$-$AA_1$-$AA_2$-$P_2$. Coupling is accomplished by activating the C-terminus of $AA_2$-$P_2$ and condensation with the amine of $P_1$-$AA_1$. Activating reagents and coupling conditions are well known to one of skill in the art and include carbodiimide mediated coupling or formation of N-hydroxysuccinimide esters followed by acylation. For synthesis of the dipeptidic hydroxamic acids, protecting group removal and N-terminal functionalization with $R^7$—Z—L (in either order) is effected to give a dipeptide precursor that is converted to a hydroxamic compound of the invention, typically by treatment with hydroxylamine. For synthesis of the tripeptidic hydroxamic acids, compound $P_1$-$AA_1$-$AA_2$-$P_2$ is selectively N-deprotected to give $P_1$-$AA_1$-$AA_2$ which is then coupled to an N-protected amino acid $AA_3$-$P_3$. Deprotection, N-terminal functionalization and treatment with hydroxylamine as shown in Scheme B then gives tripeptide hydroxamic acids of Formula I.

Scheme A
Synthesis of dipeptidic hydroxamic acids

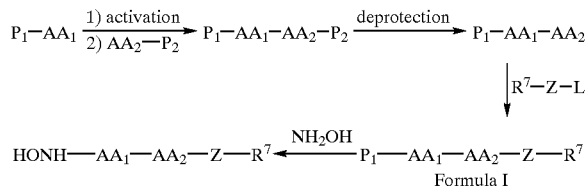

Scheme B
Synthesis of tripeptidic hydroxamic acids

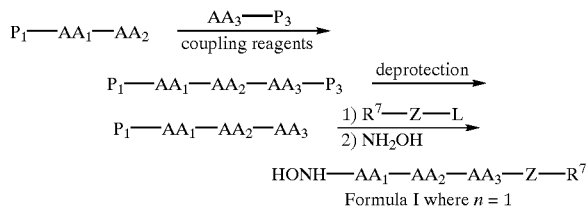

With reference to the nomenclature in Formula I, $AA_1$ corresponds to —C(=O)—$CR^1R^2$—$NR^3$—, $AA_2$ corresponds to —C(=O)—$CR^4R^5$—$NR^6$— and $AA_3$ corresponds to —C(=O)—CH($R^9$)—(CH$_2$)$_m$—$NR^{10}$. $P_1$, $P_2$ and $P_3$ represent protecting groups.

In particular, compounds of this invention may be prepared by solid phase synthesis. Initially, an N-protected amino acid $P_1$-$AA_1$ is attached to a solid phase resin via its C-terminus. Typical solid phase resins include chloromethylated and hydroxymethylated resins such as the 4-hydroxymethyl-phenylacetamidomethyl resin (Pam resin) and the 4-benzyloxybenzyl alcohol resin (Wang resin) available from Advanced Chemtech, Louisville, Ky., U.S.A. and the pegylated polystyrene resin, ArgoGel-OH™, resin from Argonaut Technologies Inc. (Belmont, Calif.). Preferred chloromethyl resins include the styrene/divinylbenzene resins known as Merrifield resins available from Aldrich Chemical Company, Milwaukee, Wis., U.S.A.

Amino acid building blocks, $AA_2$ and $AA_3$ are then attached sequentially using iterative coupling and deprotection steps well known to one of skill in the art. Coupling reactions are done under conventional peptide coupling conditions, typically in an anhydrous inert aprotic polar solvent (e.g. dimethyl formamide, acetonitrile, tetrahydrofuran, dichloromethane etc.) using auxiliary coupling reagents, e.g., carbodiimides such as 1-ethyl-3-(3-dimethylaminopropyl)carbodiimide (EDAC), diisopropyl-carbodiimide (DIC), diimidazoles such as carbonyldiimidazole, triazoles such as hydroxybenzotriazole (HOBT) or other carboxyl activating groups such as N-hydroxysuccinimide, in the presence of an tertiary organic base such 4-dimethylaminopyridine, N-methylmorpholine or triethylamine.

The protecting groups employed depend on the group being protected and are also known to those of skill in the art. Representative protecting groups may be found in *Protective Groups in Organic Chemistry*, J. F. W. McOmie (London, Plenum Press, (1973)) and *Protective Groups in Organic Chemistry*, T. W. Greene and P. G. Wuts (John Wiley and Sons, (1991)). A favoured N-protecting group is the fluorenylmethoxycarbonyl (FMOC) group.

After assembly of the entire peptide skeleton, the protecting group at the N-terminus is removed. In certain cases the N-terminal protecting group may correspond to $ZR^7$, obviating the need for protecting group removal. Functionalization at the N-terminus is effected by subsequent treatment with a compound $R^7$—Z—L, where L is a leaving group under nucleophilic displacement conditions. The conditions used for protecting group removal vary depending on the protecting group. Acid sensitive protecting groups such as tert-butoxycarbonyl (t-BOC) are removed with mild acid (e.g trifluoroacetic acid) whereas base sensitive protecting groups such as 9-fluorenylmethoxycarbonyl (FMOC) are removed with mild organic base. Typical leaving groups L include halo, tosylate and mesylate.

Finally cleavage off the solid phase is accomplished by treatment with hydroxylamine to give compounds of Formula I.

As stated above, both natural and unnatural amino acids may be used in preparing the compounds of this invention. The natural amino acids and their abbreviations are well known and will not be repeated here. Some examples of unnatural amino acids and their abbreviations include, homoserine (hSer), homoserine lactone (hSerlac), homocysteine (Hcy), homoarginine (hArg), homocitrulline (Hci), penicillamine (Pen), Nα-methylarginine (N-MeArg), norleucine (Nle), norvaline (Nval), norisoleucine (NIle), N-methylisoleucine (N-MeIle), phenylglycine (PhG), t-butylglycine (Tle), hydroxyproline (Hyp), 3,4-dehydroproline (Δ-Pro), pyroglutamine (Pyr,Glp), ornithine (Orn), 2,3-diaminopropionic acid (2,3-DAP), 1-aminoisobutyric acid (1-Aib), 2-aminoisobutyric acid (2-Aib), 2-aminobutyric acid (2-Abu), 4-aminobutyric acid (4-Abu), 2,4-diaminobutyric acid (A2bu), α-aminosuberic acid (Asu), albizzin (Abz), β-cyclohexylalanine (Cha), 3-(1-naphthyl)alanine (1-Nal), 3-(2-naphthyl)alanine (2-Nal), citrulline (Cit). pipecolinic acid (Pip), 4-chlorophenylalanine (4-ClPhe), 4-fluorophenylalanine (4-FPhe), sarcosine (Sar), 4-thiazolylalanine (4-Taz), homophenylalanine (Hpa or hPhe), 2-thienylalanine (2-Thi), 3-benzothienylalanine (3-Bal), and 1-aminopropanecarboxylic acid (1-NCPC). A variety of unnatural amino acids are available from commercial vendors.

Utility, Testing, and Administration

Utility

Compounds of this invention are useful to treat diseases associated with the excessive deposition of interstitial collagens, such as fibroproliferatives diseases exemplified by interstitial pulmonary fibrosis, pericentral fibrosis, Symmers' fibrosis, perimuscular fibrosis, kidney fibrosis, endocardial sclerosis, hepatitis, acute respiratory distress syndrome, arthritis, cystic fibrosis, surgical adhesions, tendon surgery, corneal scarring, scleroderma, chronic allograft rejection, hemodialysis shunt fibrosis and restenosis.

Compounds of this invention are inhibitors of procollagen C-proteinase and thereby inhibit the C-terminal processing of types I, II and III collagens necessary for their ability to form insoluble collagen fibrils. Furthermore, selected compounds of the invention selectively inhibit procollagen C-proteinase over other collagen degrading enzymes such as collagenase-1, collagenase-2 and collagenase-3. As a result, compounds of this invention leave largely unaffected the natural resorption of collagen mediated by collagenase-1, collagenase-2 and collagenase-3. Due to this selectivity, such compounds are of greater therapeutic efficacy than nonselective inhibitors. In particular, preferred compounds of this invention inhibit procollagen C-proteinase with greater than 100 fold selectivity over collagenase-1 and collagenase-2 and the most selective compounds are more than a thousand fold more selective. Selective inhibition of procollagen C-proteinase over collagenase-1 and collagenase-2 was demonstrated by the assays described in the Examples. Thereby, this invention allows the treatment of fibrotic diseases by administering to a patient an agent that selectively inhibits procollagen C-proteinase over collagenase-1, collagenase-2 and collagenase-3. The inhibition may be 10 fold more selective, preferably 100 fold more selective and most preferably 1000 fold more selective.

Testing

The ability of the compounds of Formula (I) to inhibit procollagen C-proteinase activity, may be demonstrated by a variety of in vitro assays known to those of ordinary skill in the art, such as the assay described in more detail in Example XIII. The selectivity against collagenase enzymes may be determined by testing as described in Example XIV.

The in vivo efficacy of compounds of Formula (I) against fibrotic disease and the overproduction and deposition of collagen may be shown by numerous animal models including the mouse bleomycin induced pulmonary fibrosis model (S. H. Phan et. al. "Bleomycin-induced Pulmonary Fibrosis," Am. Rev. Respir. Dis., 124:428–434 (1981) and P. F. Piguet et al. "Effective Treatment of the Pulmonary Fibrosis Elicited in Mice by Bleomycin or Silica with anti-CD-11 Antibodies," Am. Rev. Resp. Dis., 147:435–441 (1993)) the sponge implant model (E. N. Unemori et al. "Human Relaxin Decreases Collagen Accumulation In Vivo in Two Rodent Models of Fibrosis," J. Invest. Dermatol., 101:280–285 (1993), the carbon tetrachloride or NDMU induced renal fibrosis model, as well as other animal models cited in WO 97/05865 ("C-Proteinase Inhibitors for the Treatment of Disorders Relating to the Overproduction of Collagen"), published Feb. 20, 1997.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day.

Therapeutically effective amounts of compounds of formula I may range from approximately 0.05–35 mg per kilogram body weight of the recipient per day; preferably about 0.3–20 mg/kg/day. Thus, for administration to a 70 kg person, the dosage range would most preferably be about 21 mg to 1.4 g per day.

In general, compounds of this invention will be administered as pharmaceutical compositions by any one of the following routes: oral, systemic (e.g., transdermal, intranasal, pulmonary or by suppository), or parenteral (e.g., intramuscular, intravenous or subcutaneous) administration. The preferred manner of administration is systemic using a convenient daily dosage regimen which can be adjusted according to the degree of affliction.

Intranasal delivery is typically accomplished with dry powder formulations, liquid solutions or suspensions suitable for nebulization or with aerosol propellants suitable for use in a metered dose inhaler. Alternatively, drug substance may be associated with microspheres made of materials such as gelatin, dextran, collagen or albumin. The microspheres are conveniently delivered in freeze dried form with a nasal insufflator device or a pressurized aerosol cannister. Penetration enhancers such as amphiphilic steroids may also be used as additives to increase the systemic absorption of the drug into the tissue.

Effective administration may also be accomplished by pulmonary or respiratory delivery since polypeptides are readily absorbed through the cellular lining of the alveolar region of the mammalian lung. Advantageously, such administration frequently does not require the use of penetration enhancers as additives. Devices and methods for pulmonary delivery deep into the lung are described in U.S. Pat. No. 5,780,014, issued Jul. 14, 1998 and U.S. Pat. No. 5,814,607, issued Sep. 29, 1998.

Lastly, compounds may be systemically administered by transdermal delivery, which typically involves placing the drug on the surface of the skin and allowing it to permeate through the skin. Transdermal delivery devices employ a structure such as an adhesive patch or the like that serves as a reservoir for the drug and brings the drug into diffusive contact with the skin. In one general typ, the structure is a three dimensionally stable matrix known as a monolithic matrix. Such matrices are described in more detail in U.S. Pat. Nos. 5,804,214, 5,149,538 and 4,956,171 which describe matrices made of polymers and copolymers of acrylic latexes, acrylic esters, methacrylic esters and vinyl acetates.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of formula (I) in combination with at least one pharmaceutically acceptable excipient. Acceptable excipients are non-toxic, aide administration, and do not adversely affect the therapeutic benefit of the compound of formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in *Remington's Pharmaceutical Sciences*, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01–99.99 wt % of a compound of formula I based on the total formulation, with the balance being one or more suitable pharmaceutical excipients. Preferably, the compound is present at a level of about 1–80 wt %. Representative pharmaceutical formulations containing a compound of formula I are described in Example 30.

EXAMPLES

The following preparations and examples are given to enable those skilled in the art to more clearly understand and to practice the present invention. They should not be considered as limiting the scope of the invention, but merely as being illustrative and representative thereof. $Ac_2O$ capping solution—19 mL $Ac_2O$, 9 mL DIPEA, 0.8 eq. HOBt, 400 mL NMP Abbreviations $Ac_2O$—acetic anhydride
DIPEA—diisopropylethylamine
HOBt—hydroxybenzotriazole
NMP—N-Methylpyrrolidinone
FMOC—Fluorenylmethoxycarbonyl
BOC—t-butoxycarbonyl
DIC—diisopropylcarbodiimide
DMAP—4-dimethylaminopyridine
HATU—O-(7-azabenzotriazol-1-yl)-1,1,3,3-tetramethyluronium hexafluorophosphate]
HOAT—1-hydroxy-7-azabenzotriazole
TFA—trifluoroacetic acid
DMF—dimethylformamide
TIS—triisopropylsilane
CBz—benzyloxycarbonyl
THF—tetrahydrofuran
Taz—4-thiazolylalanine
Ile—isoleucine
Su—succinimidyl
TEA—triethylamine
Trp—tryptophan
DMSO—dimethylsulfoxide
TMS—trimethylsilyl
DMEM-HG—Dulbeccos Modified Eagle Medium, high glucose
G418—Geniticin Synthesis of Compounds of Formula I Compounds of Formula (I) were made by solid phase synthesis using conventional methods as generally described in the following Examples. If necessary, the compounds prepared as described in Examples I–X were purified by reverse phase high pressure liquid chromatography on silica gel bonded diisopropylphenethylsilane columns (Zorbax SB-Phenyl) using gradient elution with a mixed acetonitrile-water (1% TFA) solvent system at flow rates of approximately 1.5–2.0 mL/minute. They were directly tested in the PCP and collagenase assays described in Examples XIII and XIV without further purification. The compounds may be characterized using conventional means, including physical constants and spectral data. In particular, they were analyzed by mass spectrometry using electron spray ionization.

Example I

General Experimental for $CBz-AA_2-AA_1-NHOH$

Dipeptide Compounds of Formula I where $ZR^7$ is benzyloxycarbonyl

1. $BOC-AA_1$ or $FMOC-AA_1$

To ArgoGel-OH™ (Argonaut Technologies, Belmont, Calif.) in a empty solid phase extraction vial, fitted with a stopcock was added 3 eq. of either BOC or FMOC protected $AA_1$, 3 eq. of diisopropylcarbodiimide and 0.05 eq. of a 0.116 M solution of dimethylaminopyridine in THF. Sufficient $CH_2Cl_2$ was added to swell the resin (~12.5 mL/gr of resin). [Alternatively, to the resin was added 3 eq. of either BOC or FMOC protected $AA_1$, 3 eq. of HATU, 3 eq. HOAt and 6 eq. of DIPEA. Sufficient NMP was added to swell the resin (~12.5 mL/gr of resin).] The reaction was then placed on a spinner and rotated overnight. The reaction was then filtered by suction filtration and washed three times with $CH_2Cl_2$, three times with MeOH, once with 1:1 HOAc/$CH_2Cl_2$, three times with MeOH and then lastly three times with $CH_2Cl_2$ and dried to give $BOC-AA_1$-resin or $FMOC-AA_1$ resin. The unreacted resin sites were then capped off with an $Ac_2O$ capping solution (19 mL $Ac_2O$, 9 mL DIPEA, 0.8 gr HOBt, 400 mL NMP) in a sufficient quantity added to swell the resin (~12.5 mL/gr of resin). The resin was then filtered and washed as above.

2. $H_2N-AA_1$-resin

2a. For BOC protected material—The resulting resin from above ($BOC-AA_1$-resin) was treated with a solution of 95/2.5/2.5 $TFA/H_2O$/triisopropyl silane (TIS) for two hours. The reaction was then filtered by suction filtration and washed three times with $CH_2Cl_2$, three times with MeOH, and then three times with $CH_2Cl_2$ to give $H_2N-AA_1$-resin.

2b. For FMOC protected material—The resulting resin from above ($FMOC-AA_1$-resin) was first washed with DMF then treated with a solution of 20% piperidine in DMF for 20 min. The reaction was then filtered by suction filtration and washed three times with $CH_2Cl_2$, three times with MeOH, once with 1:1 HOAc/$CH_2Cl_2$, three times with MeOH and then lastly three times with $CH_2Cl_2$, to give $H_2N-AA_1$-resin.

3. $CBz-AA_2-AA_1$ resin

To $H_2N-AA_1$-resin was added 3 eq. of CBZ protected $AA_2$, 3 eq. of diisopropylcarbodiimide and 0.05 eq. of a 0.116 M solution of dimethylaminopyridine in THF. Sufficient $CH_2Cl_2$ was added to swell the resin (~12.5 mL/gr of resin). [Alternatively, to the resin was added 3 eq. of CBz protected $AA_2$, 3 eq. of HATU, 3 eq. HOAt and 6 eq. of DIPEA. Sufficient NMP is added to swell the resin (~12.5 mL/gr of resin ).] The reaction was then placed on a spinner and rotated overnight. The reaction was then filtered by suction filtration and washed three times with $CH_2Cl_2$, three times with MeOH, once with 1:1 $HOAc/CH_2Cl_2$, three times with MeOH and then lastly three times with $CH_2Cl_2$ to give $CBz-AA_2-AA_1$-resin.

4. Removal of Protecting Groups

If $AA_1$ or $AA_2$ contains an acid labile side chain protecting group that is to be removed, the resulting resin ($CBz-AA_2-AA_1$-resin) was treated with a solution of 95/2.5/2.5 $TFA/H_2O$/triisopropyl silane (TIS) for 2 hours. The reaction was then filtered by suction filtration and washed three times with $CH_2Cl_2$, three times with MeOH, and then three times with $CH_2Cl_2$.

5. $CBz-AA2-AA_1$-NHOH $CBz-AA_2-AA_1$-resin was first washed with THF. Sufficient THF was added to swell the resin (~12.5 mL/gr of resin) then 25 eq. of 50% aq. $NH_2OH$ was added and the reaction was rotated for two days. The reaction was then filtered by suction filtration and washed with $CH_2Cl_2$, MeOH, and then $CH_2Cl_2$. The filtrate was concentrated under vacuum to obtain $CBz-AA_2-AA_1$-NHOH.

Example II

General Experimental for $R^7-SO_2-AA_2-AA_1$-NHOH

Dipeptide Compounds of Formula I where Z is
—$SO_2$—

1. $FMOC-AA_2-AA_1$-resin

To $H_2N-AA_1$-resin was added 3 eq. of FMOC protected $AA_2$, 3 eq. of diisopropylcarbodiimide and 0.05 eq. of a 0.116 M solution of 4-dimethylaminopyridine in THF. Sufficient $CH_2Cl_2$ was added to swell the resin (~12.5 mL/gr of resin). The reaction was then placed on a spinner and rotated overnight. The reaction was then filtered by suction filtration and washed three times with $CH_2Cl_2$, three times with MeOH, once with 1:1 $HOAc/CH_2Cl_2$, three times with MeOH and then lastly three times with $CH_2Cl_2$, to give $FMOC-AA_2-AA_1$-resin.

2. $H_2N-AA_2-AA_1$-resin $FMOC-AA_2-AA_1$-resin was first washed with DMF then treated with a solution of 20% piperidine in DMF for 20 min. The reaction was then filtered by suction filtration and washed three times with $CH_2Cl_2$, three times with MeOH, once with 1:1 $HOAc/CH_2Cl_2$, 3 times with MeOH and then lastly 3 times with $CH_2Cl_2$, to give $H_2N-AA_2-AA_1$-resin.

3. $R^7-SO_2-AA_2-AA_1$-resin $H_2N-AA_2-AA_1$-resin was first washed with aq. dioxane, then 10 eq. of the desired sulfonyl chloride, $R^7-SO_2Cl$, was added. Sufficient 90% aq. dioxane was added to swell the resin (~12.5 mL/gr of resin). Then 20 eq. of diisopropylethylamine was added. The reaction was then placed on a spinner and rotated overnight. The reaction was then filtered by suction filtration and washed three times with $CH_2Cl_2$, three times with MeOH, once with 1:1 $HOAc/CH_2Cl_2$, three times with MeOH and then lastly three times with $CH_2Cl_2$ to give $R^7-SO_2-AA_2-AA_1$-resin.

4. $R^7-SO_2-AA_2-AA_1$-NHOH $R^7-SO_2-AA_2-AA_1$-resin was first washed with THF. Sufficient THF was added to swell the resin (~12.5 mL/gr of resin) then 25 eq. of 50% aq. $NH_2OH$ was added and the reaction was rotated for two days. The reaction was then filtered by suction filtration and washed with $CH_2Cl_2$, MeOH, and then $CH_2Cl_2$. The filtrate was concentrated under vacuum to obtain $R^7-SO_2-AA_2-AA_1$-NHOH.

Example III

General Experimental for $R^7NHCO-AA_2-AA_1$-NHOH

Dipeptide Compounds of Formula I where Z is
—CONH—

1. $R^7-NHCO-AA_2-AA_1$-resin $H_2N-AA_2-AA_1$-resin was first washed with THF, then 3 eq. of the desired isocyanate, $R^7N=C=O$, was added. Sufficient THF was added to swell the resin (~12.5 mL/gr of resin). The reaction was then placed on a spinner and rotated overnight. The reaction was then filtered by suction filtration and washed three times with $CH_2Cl_2$, three times with MeOH, once with 1:1 $HOAc/CH_2Cl_2$, three times with MeOH and then lastly three times with $CH_2Cl_2$ to give $R^7-NHCO-AA_2-AA_1$-resin.

2. Removal of Protecting Groups

If $AA_1$ or $AA_2$ contains an acid labile side chain protecting group that is to be removed, the resulting resin ($R^7-NHCO-AA_2-AA_1$-resin) was treated with a solution of 95/2.5/2.5 $TFA/H_2O$/ triisopropyl silane (TIS) for 2 hours. The reaction was then filtered by suction filtration and washed three times with $CH_2Cl_2$, three times with MeOH, and then three times with $CH_2Cl_2$.

3. $R^7-NHCO-AA_2-AA_1$-NHOH $R^7NHCO-AA_2-AA_1$-resin was first washed with THF. Sufficient THF was added to swell the resin (~12.5 mL/gr of resin) then 25 eq. of 50% aq. $NH_2OH$ was added and the reaction was rotated for two days. The reaction was then filtered by suction filtration and washed with $CH_2Cl_2$, MeOH, and then $CH_2Cl_2$. The filtrate was concentrated under vacuum to obtain $R^7NHCO-AA_2-AA_1$-NHOH.

The dipeptide hydroxamic acids in Table II and Table V where Z is —CONH— were prepared using the procedure of Example 3.

Example IV

General Experimental for $R^7-CO-AA_2-AA_1$-NHOH

Dipeptide Compounds of Formula I where Z is
—CO—

1. $R^7-CO-AA_2-AA_1$-resin

To $H_2N-AA_2-AA_1$-resin was added sufficient $CH_2Cl_2$ to swell the resin (~12.5 mL/gr of resin). 3 eq. of the desired acid chloride, $R^7COCl$, and 3 eq. of $Et_3N$ were then added. A second alternative was add to the $CH_2Cl_2$ swollen resin 3 eq. of the desired carboxylic acid, $R^7CO_2H$, 3 eq. of diisopropylcarbodiimide and 0.05 eq. of a 0.116 M solution of dimethylaminopyridine in THF. A third alternative was to swell the resin with sufficient $CH_3CN$ (~12.5 mL/gr of resin) and couple the desired acid chloride, $R^7COCl$ (3 eq.) in the presence of 6 eq. of trimethylsilylcyanide. In all cases the reaction was then placed on a spinner and rotated overnight. The reaction was then filtered by suction filtration and washed three times with $CH_2Cl_2$, three times with MeOH, once with 1:1 $HOAc/CH_2Cl_2$, three times with MeOH and then lastly three times with $CH_2Cl_2$ to give $R^7-CO-AA_2-AA_1$-resin.

2. Removal of Protecting Groups

If $AA_1$ or $AA_2$ contains an acid labile side chain protecting group that is to be removed, the resulting resin ($R^7-CO-AA_2-AA_1$-resin) was treated with a solution of 95/2.5/2.5

TFA/H$_2$O/triisopropyl silane (TIS) for 2 hours. The reaction was then filtered by suction filtration and washed three times with CH$_2$Cl$_2$, three times with MeOH, and then three times with CH$_2$Cl$_2$.

3. R$^7$-CO-AA$_2$-AA$_1$-NHOH

R$^7$-CO-AA$_2$-AA$_1$-resin was first washed with THF. Sufficient THF was added to swell the resin (~12.5 mL/gr of resin) then 25 eq. of 50% aq. NH$_2$OH was added and the reaction was rotated for two days. The reaction was then filtered by suction filtration and washed with CH$_2$Cl$_2$, MeOH, and then CH$_2$Cl$_2$. The filtrate is concentrated under vacuum to obtain R$^7$-CO-AA$_2$-AA$_1$-NHOH.

Example V

General Experimental for R$^7$-OC(=O)-AA$_2$-AA$_1$-NHOH

Dipeptide Compounds of Formula I where Z is —C(O)O—

1. R$^7$-OCO-AA$_2$-AA$_1$-resin.

To H$_2$N-AA$_2$-AA$_1$-resin was added 3 eq. of the desired succinimidylcarbonate, R$^7$OC(=O)NHS, 3 eq. Et$_3$N and and 0.05 eq. of a 0.116 M solution of 4-dimethylaminopyridine in THF. Sufficient CH$_2$Cl$_2$ was added to swell the resin (~12.5 mL/gr of resin). Another alternative was to add to the resin 10 eq. of the desired chloroformate, R$^7$OCOCl, and 20 eq. diisopropylethylamine followed by sufficient 90% aq. dioxane to swell the resin (~12.5 mL/gr of resin)]. In either case, the reaction was then placed on a spinner and rotated overnight. The reaction was then filtered by suction filtration and washed three times with CH$_2$Cl$_2$, three times with MeOH, once with 1:1 HOAc/CH$_2$Cl$_2$, three times with MeOH and lastly three times with CH$_2$Cl$_2$ to give R$^7$-OCO-AA$_2$-AA$_1$-resin.

2. Removal of Protecting Groups

If AA$_1$ or AA2 contains an acid labile side chain protecting group that is to be removed, the resulting resin (R$^7$-OCO-AA$_2$-AA$_1$-resin) was treated with a solution of 95/2.5/2.5 TFA/H$_2$O/triisopropyl silane (TIS) for 2 hours. The reaction was then filtered by suction filtration and washed three times with CH$_2$Cl$_2$, three times with MeOH, and then three times with CH$_2$Cl$_2$.

3. R$^7$-OCO-AA$_2$-AA$_1$-NHOH

R$^7$-OCO-AA$_2$-AA$_1$-resin was first washed with THF. Sufficient THF was added to swell the resin (~12.5 mL/gr of resin) and 25 eq. of 50% aq. NH$_2$OH is added and the reaction was rotated for two days. The reaction was then filtered by suction filtration and washed with CH$_2$Cl$_2$, MeOH, and then CH$_2$Cl$_2$. The filtrate was concentrated under vacuum to obtain R$^7$-OCO-AA$_2$-AA$_1$-NHOH.

Example VI

General Experimental for CBz-NR$^6$-CH$_2$CO-AA$_1$-NHOH

1. BrCH$_2$CO-AA$_1$-resin

To H$_2$N-AA$_1$-resin was added 12 eq. of bromoacetic acid and 13 eq. of diisopropylcarbodiimide. Sufficient CH$_2$Cl$_2$ was added to swell the resin (~12.5 mL/gr of resin). The reaction was then placed on a spinner and rotated for 2 hrs. The reaction was filtered by suction filtration and washed three times with CH$_2$Cl$_2$, three times with DMSO and lastly three times with CH$_2$Cl$_2$ to give BrCH$_2$CO-AA$_1$-resin.

2. R$^6$-NHCH$_2$CO-AA$_1$-resin

BrCH$_2$CO-AA$_1$-resin was first washed with DMSO. Sufficient DMSO was added to swell the resin (~12.5 mL/gr of resin) followed by the addition of 40 eq. of the desired primary amine, R$^6$NH$_2$. The reaction was then placed on a spinner and rotated overnight. The reaction was then filtered by suction filtration and washed three times with CH$_2$Cl$_2$, three times with MeOH, once with 1:1 HOAc/CH$_2$Cl$_2$, three times with MeOH and then lastly three times with CH$_2$Cl$_2$ to give R$^6$-NHCH$_2$CO-AA$_1$-resin.

3. CBz-NR$^6$-CH$_2$CO-AA$_1$-resin

To R$^6$-NHCH$_2$CO-AA$_1$-resin is added 3 eq. of CBZOSu, 3 eq. Et$_3$N and 0.05 eq. of a 0.116 M solution of 4-dimethylaminopyridine in THF. Sufficient CH$_2$Cl$_2$ was added to swell the resin (~12.5 mL/gr of resin). The reaction was then placed on a spinner and rotated overnight. The reaction was then filtered by suction filtration and washed three times with CH$_2$Cl$_2$, three times with MeOH, once with 1:1 HOAc/CH$_2$Cl$_2$, three times with MeOH and lastly three times with CH$_2$Cl$_2$ to give CBz-NR$^6$-CH$_2$CO-AA$_1$-resin.

4. Removal of Protecting Groups

If AA$_1$ or AA2 contains an acid labile side chain protecting group that is to be removed, the resulting resin (CBz-NR$^6$-CH$_2$CO-AA1-resin) was treated with a solution of 95/2.5/2.5 TFA/H$_2$O/triisopropyl silane (TIS) for 2 hours. The reaction was then filtered by suction filtration and washed three times with CH$_2$Cl$_2$, three times with MeOH, and then three times with CH$_2$Cl$_2$.

5. CBz-NR$^6$-CH$_2$CO-AA$_1$-NHOH

CBz-NR$^6$-CH$_2$CO-AA$_1$-resin was first washed with THF. Sufficient THF was added to swell the resin (~12.5 mL/gr of resin) and then 25 eq. of 50% aq. NH$_2$OH was added and the reaction was rotated for two days. The reaction was then filtered by suction filtration and washed with CH$_2$Cl$_2$, MeOH and finally CH$_2$Cl$_2$. The filtrate was concentrated under vacuum to obtain CBz—NR$^6$-CH$_2$CO-AA$_1$-NHOH.

Example VII

General Experimental for R$^7$NHCO-AA$_2$-AA$_1$-NHOH

Dipeptide Compounds of Formula I where Z is —C(O)NH—

1. To ArOCO-AA$_2$-AA$_1$-resin (Ar=Ph) was added sufficient DMF to swell the resin (~12.5 mL/gr of resin). 20 eq. of R$^7$NH$_2$ was added and the reaction reaction was then placed on a spinner and rotated overnight. The reaction was then filtered by suction filtration and washed three times with CH$_2$Cl$_2$, three times with MeOH, once with 1:1 HOAc/CH$_2$Cl$_2$, three times with MeOH and then lastly three times with CH$_2$Cl$_2$ to give R$^7$NHCO-AA$_2$-AA$_1$-resin.

2. R$^7$NHCO-AA$_2$-AA$_1$-resin was first washed with THF. Sufficient THF was added to swell the resin (~12.5 mL/gr of resin), then 25 eq. of 50% aq. NH$_2$OH was added and the reaction was rotated for two days. The reaction was then filtered by suction filtration and washed with CH$_2$Cl$_2$, MeOH, and then CH$_2$Cl$_2$. The filtrate was concentrated under to obtain R$^7$NHCO-AA$_2$-AA$_1$-NHOH.

Example VIII

General Experimental for CBz-AA$_3$-AA$_2$-AA$_1$-NHOH

Tripeptide Compounds of Formula I where n=1 and ZR$^7$ is benzyloxycarbonyl

1. CBz-AA$_3$-AA$_2$-AA$_1$-resin

To H$_2$N-AA$_2$-AA$_1$-resin was added three eq. of CBZ protected AA$_3$, three eq. of diisopropylcarbodiimide and 0.05 eq. of a 0.116 M solution of dimethylaminopyridine in THF. Sufficient $CH_2Cl_2$ is added to swell the resin (~12.5 mL/gr of resin). [An alternative is to add to the resin three eq. of CBz protected $AA_3$, three eq. of HATU, three eq. HOAt and six eq. of DIPEA. Sufficient NMP was added to swell the resin (~12.5 mL/gr of resin).] The reaction was placed on a spinner and rotated overnight. The reaction was filtered by suction filtration and washed three times with $CH_2Cl_2$, three times with MeOH, once with 1:1 HOAc/$CH_2Cl_2$, three times with MeOH and lastly three times with $CH_2Cl_2$, to give CBz-$AA_3$-$AA_2$-$AA_1$-resin.

2. Removal of Protecting Groups

If $AA_1$, $AA_2$ or $AA_3$ contains an acid labile side chain protecting group that is to be removed, the resulting resin (CBz-$AA_3$-$AA_2$-$AA_1$-resin) was treated with a solution of 95/2.5/2.5 TFA/$H_2O$/triisopropyl silane (TIS) for 2 hours. The reaction was then filtered by suction filtration and washed three times with $CH_2Cl_2$, three times with MeOH, and then three times with $CH_2Cl_2$.

3. CBz-$AA_3$-$AA_2$-$AA_1$-NHOH

CBz-$AA_3$-$AA_2$-$AA_1$-resin was first washed with THF. Sufficient THF was added to swell the resin (~12.5 mL/gr of resin) then 25 eq. of 50% aq. $NH_2OH$ was added and the reaction was rotated for two days. The reaction was filtered by suction filtration and washed with $CH_2Cl_2$, MeOH, and finally with $CH_2Cl_2$. The filtrate was concentrated under vacuum to obtain CBz-$AA_3$-$AA_2$-$AA_1$-NHOH.

Example IX

General Experimental for $R^7Z$-$AA_3$-$AA_2$-$AA_1$-NHOH

Tripeptide Compounds of Formula I where Z is —$SO_2$— or —C(O)NH—

1. FMOC-$AA_3$-$AA_2$-$AA_1$-resin

To $H_2N$-$AA_2$-$AA_1$-resin was added three eq. of FMOC protected $AA_3$, three eq. of diisopropylcarbodiimide and 0.05 eq. of a 0.116 M solution of 4-dimethylaminopyridine in THF. Sufficient $CH_2Cl_2$ was added to swell the resin (~12.5 mL/gr of resin). [and alternative was to add to the resin three eq. of FMOC protected $AA_3$, three eq. of HATU, three eq. HOAt and six eq. of DIPEA. Sufficient NMP was added to swell the resin (~12.5 mL/gr of resin ).] The reaction was placed on a spinner and rotated overnight. The reaction was then filtered by suction filtration and washed three times with $CH_2Cl_2$, three times with MeOH, once with 1:1 HOAc/$CH_2Cl_2$, three times with MeOH and then lastly three times with $CH_2Cl_2$ to give FMOC-$AA_3$-$AA_2$-$AA_1$-resin.

2. $H_2N$-$AA_3$-$AA_2$-$AA_1$-resin

FMOC-$AA_3$-$AA_2$-$AA_1$-resin was first washed with DMF then treated with a solution of 20% piperidine in DMF for 20 min. The reaction was then filtered by suction filtration and washed three times with $CH_2Cl_2$, three times with MeOH, once with 1:1 HOAc/$CH_2Cl_2$, three times with MeOH and then lastly three times with $CH_2Cl_2$ to give $H_2N$-$AA_3$-$AA_2$-$AA_1$-resin.

3. $R^7Z$-$AA_3$-$AA_2$-$AA_1$-resin

3a. For Z=$SO_2$: $H_2N$-$AA_3$-$AA_2$-$AA_1$-resin is first washed with aq. dioxane, then 10 eq. of the desired sulfonyl chloride, $R^7SO_2Cl$ is added followed by sufficient 90% aq. dioxane to swell the resin (~12.5 mL/gr of resin). Then 20 eq. of diisopropylethylamine was added. The reaction was then placed on a spinner and rotated overnight. The reaction was then filtered by suction filtration and washed three times with $CH_2Cl_2$, three times with MeOH, once with 1:1 HOAc/$CH_2Cl_2$, three times with MeOH and then lastly three times with $CH_2Cl_2$ to give $R^7SO_2$-$AA_3$-$AA_2$-$AA_1$-resin.

3b. For Z=NHCO: $H_2N$-$AA_3$-$AA_2$-$AA_1$-resin was first washed with THF and then three eq. of the desired isocyanate, $R^7N$=C=O was added followed by sufficient THF to swell the resin (~12.5 mL/gr of resin). The reaction was then placed on a spinner and rotated overnight. The reaction was then filtered by suction filtration and washed three times with $CH_2Cl_2$, three times with MeOH, once with 1:1 HOAc/$CH_2Cl_2$, three times with MeOH and then lastly three times with $CH_2Cl_2$ to give $R^7NHCO$-$AA_3$-$AA_2$-$AA_1$-resin.

4. $R^7Z$-$AA_3$-$AA_2$-$AA_1$-NHOH $R^7Z$-$AA_3$-$AA_2$-$AA_1$-resin is first washed with THF. Sufficient THF is added to swell the resin (~12.5 mL/gr of resin) then 25 eq. of 50% aq. $NH_2OH$ is added and the reaction is rotated for two days. The reaction is then filtered by suction filtration and washed with $CH_2Cl_2$, MeOH, and then $CH_2Cl_2$. The filtrate is concentrated on a Speed Vac to obtain $R^7Z$-$AA_3$-$AA_2$-$AA_1$-NHOH.

Example X

General Experimental for $R^7Z$—$NR^{10}C(O)CH_2$-$AA_2$-$AA_1$-NHOH

Tripeptide Compounds of Formula I where n=1, m=0, $R^9$ is hydrogen (A is $C(O)CH_2NR^{10}$ and Z is a bond, —$SO_2$—, —C=O, or —C(O)NH—

1. $BrCH_2CO$-$AA_2$-$AA_1$-resin

To $H_2N$-$AA_2$-$AA_1$-resin was added twelve eq. of bromoacetic acid and twelve eq. of diisopropylcarbodiimide. Sufficient $CH_2Cl_2$ was added to swell the resin (~12.5 mL/gr of resin). The reaction was then placed on a spinner and rotated two hrs. The reaction was then filtered by suction filtration and washed three times with $CH_2Cl_2$, three times with DMSO and then lastly three times with $CH_2Cl_2$ to give $BrCH_2CO$-$AA_2$-$AA_1$-resin.

2. $R^{10}NHCH_2CO$-$AA_2$-$AA_1$-resin $BrCH_2CO$-$AA_2$-$AA_1$-resin is first washed with DMSO. Sufficient DMSO is added to swell the resin (~12.5 mL/gr of resin) followed by the addition of 40 eq. of the desired amine, $R^{10}NH_2$ or $R^7R^{10}NH$. The reaction was then placed on a spinner and rotated overnight. The reaction was then filtered by suction filtration and three times with $CH_2Cl_2$, three times with MeOH, once with 1:1 HOAc/$CH_2Cl_2$, three times with MeOH and then lastly three times with $CH_2Cl_2$ to give $R^{10}NHCH_2CO$-$AA_2$-$AA_1$-resin or $R^7R^{10}NHCH_2CO$-$AA_2$-$AA_1$-resin. (If $R^7R^{10}NH$ is used, corresponding to Z being a bond, go directly to step 4)

3. $R^7Z$—$NR^{10}CH_2CO$-$AA_2$-$AA_1$-resin

3a. For Z=—$SO_2$—: $R^{10}NHCH_2CO$-$AA_2$-$AA_1$-resin is first washed with aq. dioxane, then 10 eq. of the desired sulfonyl chloride, $R^7SO_2Cl$, is added. Sufficient 90% aq. dioxane was added. The swell the resin (~12.5 mL/gr of resin). Then 20 eq. of diisopropylethylamine was added. The reaction was then placed on a spinner and rotated overnight. The reaction was then filtered by suction filtration and washed three times with $CH_2Cl_2$, three times with MeOH, once with 1:1 HOAc/$CH_2Cl_2$, 3 times with MeOH and then lastly three times with $CH_2Cl_2$ to give $R^7SO_2$-$NR^{10}CH_2CO$-$AA_2$-$AA_1$-resin 3b. For Z=—CO—: To $R^{10}NHCH_2CO$-$AA_2$-$AA_1$, -resin is added sufficient $CH_2Cl_2$ is added to swell the resin (~12.5 mL/gr of resin). Three eq. of the desired acid chloride, $R^7COCl$, and three eq. of $Et_3N$ are then added. [A first alternative is to add to the resin sufficient $CH_2Cl_2$ is added to swell the resin (~12.5 mL/gr of resin) followed by three eq. of the desired carboxylic acid, $R^7COOH$, 3 eq. of diisopropylcarbodiimide and 0.05 eq. of a 0.116 M solution of dimethylaminopyridine in THF. A second alternative is to add to the resin 3 eq. of the desired carboxylic acid, $R^7COOH$, 3 eq. of HATU, 3 eq. HOAt and 6 eq. of DIPEA followed by sufficient NMP is added to swell the resin (~12.5 mL/gr of resin ).] The reaction was then placed on a spinner and rotated overnight. The reaction was then filtered by suction filtration and washed three times with $CH_2Cl_2$, three times with MeOH, once with 1:1 $HOAc/CH_2Cl_2$, three times with MeOH and then lastly three times with $CH_2Cl_2$ to give $R^7CO$-$NR^{10}OCH_2$-$AA_2$-$AA_1$-resin 3c. For Z=—CONH—: $R^{10}NHCH_2CO$-$AA_2$-$AA_1$-resin is first washed with THF, then 3 eq. of the desired isocyanate, $R^7N=C=O$, was added followed by sufficient THF to swell the resin (~12.5 mL/gr of resin). The reaction was then placed on a spinner and rotated overnight. The reaction was then filtered by suction filtration and washed three times with $CH_2Cl_2$, three times with MeOH, once with 1:1 $HOAc/CH_2Cl_2$, three times with MeOH and then lastly three times with $CH_2Cl_2$ to give $R^7NHCO$-$NR^{10}CH_2$-$AA_2$-$AA_1$-resin.

4. Removal of Protecting Groups

If $AA_1$ or $AA_2$ contains an acid labile side chain protecting group that is to be removed, the resulting resin ($R^7Z$-$NR^{10}CH_2CO$-$AA_2$-$AA_1$-resin) was treated with a solution of 95/2.5/2.5 $TFA/H_2O$, triisopropyl silane (TIS) for 2 hours. The reaction was then filtered by suction filtration and washed three times with $CH_2Cl_2$, three times with MeOH, and then three times with $CH_2Cl_2$.

5. $R^7Z$-$NR^{10}C(O)CH_2$-$AA_2$-$AA_1$-NHOH $R^7Z$-$NR^{10}CH_2CO$-$AA_2$-$AA_1$-resin was first washed with THF. Sufficient THF was added to swell the resin (~12.5 mL/gr of resin) then 25 eq. of 50% aq. $NH_2OH$ was added and the reaction was rotated for two days. The reaction was then filtered by suction filtration and washed with $CH_2Cl_2$, MeOH, and then $CH_2Cl_2$. The filtrate was concentrated under vacuum to obtain $R^7Z$-$NR^{10}C(O)CH_2$-$AA_2$-$AA_1$-NHOH

*Note in all cases, all solid reagents are added followed by solvent. If the reagents are not solids, the solvent is added followed by the liquid reagents. For $AA_1$ or $AA_2$ with side chain that require deprotection this was done just prior to the $NH_2OH$ cleavage reaction. Typical amino acids with side chains requiring deprotection include Glu (OtBu), His (Boc) and Ser (OtBu).

Example XI

Isolation and Preparation of Procollagen C-Proteinase

Cloning of Human PCP and Construction of the HT-1080 Vector

Human Procollagen C-Proteinase (PCP, also known as Bone Morphogenetic Protein-1 or BMP-1) was cloned by from a human fibroblast cDNA library (Stratagene, San Diego, Calif.). Cloning was performed by PCR based on the reported nucleotide sequence (Wozney, J. M., Rosen,V., Celeste,A. J., Mitsock,L. M., Whitters,M. J., Kriz,R. W., Hewick,R. M., and Wang,E. A. (1989) direct GenBank submission accession M22488, locus HUMBMP1) using Taq polymerase, the 5' primer GCGCGCGGTACCCGC-CCCGCCAGCATGCCCGGCGTGGCCCGC-CTGCCGCTGCTGCTCGGGCTGCTGCT-GCTCCCGCGTCCCGGCCGGCCGCTGGACTTGGC CGACTACACCTATGACCTGGC (SEQ ID NO:1)(Oligo Therapeutics, Inc., Wilsonville, Oreg.), and the 3' reverse strand primer CCGCTCGAGCCTCACTGGGGGGTCCG-GTTTCTTTTCTGCACTCGGAATTTGAGCTGGTG (SEQ ID NO:2) (Gibco) to yield the entire full-length nucleotide encoding the signal sequence, propeptide, catalytic domain, and all C-terminal domains to the natural translation termination site. The PCR product was purified by gel electrophoresis using the Wizard DNA Purification Kit (Promega, Madison, Wis.) and ligated directly into the mammalian expression vector pCR3. 1 (Invitrogen, Carlsbad, Calif.) by the TA cloning method. Ligated product was used to transform E. coli strain TOP 10F' (Invitrogen, Carlsbad, Calif.) by a standard heat-shock method, and transformants were selected by restriction analysis of purified plasmid using the enzymes Hindif and BamHI. Transformants testing positive for the PCP insert were submitted for sequencing using the Perkin-Elmer/ABI system. Two clones were selected that, combined, encoded the entire amino acid sequence identical to the one predicted by Wozney et al. The two clones were recombined by restriction using the enzymes BbrI, which cleaved at a naturally occurring internal site, and EcoRV, which cleaved at the junction of the insert and vector. The excised fragments were religated into EcoRV-treated pCR3. 1. The resulting construct contained the entire coding sequence identical to that reported by Wozney et al. with the exception of two silent mutations in the signal sequence, G->A at both positions 39 and 45 counting from the translation initiation site (ATG). The completed plasmid construct was amplified in E. coli DH5a and purified using anion exchange chromatography (MaxiPrep columns from Qiagen (Valencia, Calif.) catalog #12162).

Transfection of HT-1080 and Selection of the PCP-Expressing Clone

The human fibrosarcoma line HT-1080 (ATCC) was grown in high glucose DMEM (DMEM-HG) supplemented with 10% heat-inactivated fetal bovine serum (HI-FBS) in 100 mm culture dishes (Falcon, Becton Dickenson, Franklin, N.J.) and transfected with 2 ug of purified plasmid using the standard method for Lipofectamine (Gibco, Bethesda, Md.) in serum free medium. Stable transfectants were selected by treating the plated culture with 400 ug/ml G418 (Gibco). After selection for 10 days, the adherent single colonies were picked from the plate, replated in 12-well plates and grown until confluent. Individual stable colonies were screened for PCP expression by TaqMan (Perkin-Elmer, Foster City, Calif.) analysis using equivalent amounts of total RNA, the 5' primer GACGAAGAGGAC-CTGAGGGCCTT (SEQ ID NO:3) (Perkin-Elmer, Foster City, Calif.), the 3' reverse strand primer TTCCTGGAACT-GCAGCTTTGA (SEQ ID NO:4) (Perkin-Elmer, Foster City, Calif.), and the reverse strand probe TGCCGTCT-GAGATCCACAGCCTGCT (SEQ ID NO:5) (Perkin-Elmer). A stable line, HT-1080/hPCP-23, was chosen based on the highest PCP mRNA expression level in the TaqMan screen. Stocks of the HT-1080/hPCP-23 stable line were transferred to DMEM-HG supplemented with 5% HI-FBS and 10% DMSO (no G418 added) and were slowly frozen at −70° C. overnight, then transferred to a liquid nitrogen bath for long-term storage. Revitalized HT-1080/hPCP-23 were maintained in DMEM-HG supplemented with 10% HI-FBS and 250 ug/ml G418 for no more than 7 passages. Expression of PCP for harvest was carried out by replating and growing HT-1080/hPCP-23 on rat tail type I collagen-coated plates (Falcon) in OptiMEM (Gibco) serum free medium without G418 for 24 hr.

Production of PCP in HT1080 Cells

The HT1080 cells that were transformed to produce PCP were adapted to grow in suspension in optiMEM medium (GIBCO) supplemented with 5% fetal bovine serum and 4 ml/L G418 (GIBCO). The culture was maintained at 37 C.

and the dissolved oxygen at 30%. Typically batch sizes of 10 liters were produced. When the cell density reached 4–6×10$^5$ cells/ml, the culture fluid was collected and filtered through 0.2 um membranes. Alternatively, the cell culture was perfused with fresh media at the rate of 0.8 to 1.0 culture volume/day. The density of the perfused cultures reached 1–2.5×10$^6$ cells/ml and were maintained up to two weeks with continuous harvests.

Purification of PCP from HT1080 Cells

A column packed with Dyematrex Gel Green A (Millipore, Bedford, Mass.) was equilibrated against 50 mM HEPES, pH7.2, containing 6mM CaCl$_2$ and 0.3M NaCl. After the HT1080 cell culture fluid was loaded, the column was washed with 10 column volumes of the equilibration buffer containing 1.0 M NaCl. PCP was eluted with 50 mM HEPES pH 7.2 containing 3 M NaCl, 2 M urea and 6 mM CaCl$_2$. Eluate fractions were pooled and concentrated to 150–200 mls and dialyzed against 4.0 liters of 50 mM HEPES, 6 mM CaCl$_2$, pH 7.2 overnight. The material was then centrifuged at 5,000 g for 15 minutes to remove precipitates. The PCP containing sample were stored at –20 C. until ready for further processing.

The PCP containing sample was thawed and diluted with 50 mM HEPES pH 7.2 containing 6 mM CaCl$_2$, if necessary to bring the NaCl concentration to 0.1–0.15 M The pH was adjusted to 6.7 with 2 N HCl. The protein solution was filtered through a 0.45 um filter to remove any precipitate. This preparation was then loaded onto a column packed with Q-Sepharose High Performance (Pharmacia, Piscataway, N.J.) which had been equilibrated with 5 mM HEPES pH 6.7 containing 6 mM CaCl$_2$ and 0.15 M NaCl. The PCP was not retained in the column and was therefore in the flow through fractions. The PCP was concentrated to 1 mg/ml and used for screening.

Production of PCP in Drosophila Cells

Drosophila cells which had been transformed to produce PCP were grown in bioreactors at a typical batch volume of 10 liters in SF900 II SF medium (GIBCO). The temperature was maintained at 30 C. and the dissolved oxygen at 30%. Periodically the cells were fed a cocktail consisting of glutamine, lipids and yeastolate. When cell densities reached 30–50 ×10$^6$ cells/ml, supernatants were harvested by centrifugation and concentrated by ultrafiltration using a 30 Kd membrane.

Purification of PCP from Culture Fluid from Drosophila Cells

Culture fluid from the drosophila cells was concentrated 8 fold and the pH adjusted to 7.1–7.2 if necessary. The culture fluid was centrifuged at 3000 g for 10 minutes and filtered through 0.45 um filters. The culture fluid was then loaded onto columns packed with carboxy-sulfone packing material (J. T. Baker/Mallinckrodt, Phillipsburg, N.J.) which had been equilibrated with 0.1 M NaCl, 50 mM HEPES, 6 mM CaCl$_2$, pH 7.2. After being loaded, the column was washed with 10 column volumes of the equilibration buffer. Retained proteins were eluted with a gradient of 0.1 to 1.0 M NaCl in 9 column volumes. Fractions that had PCP activity were pooled for further purification.

The PCP eluted off the carboxy-sulfone column was loaded onto a Dyematrex Gel Green A (Millipore, Bedford, Mass.) column that had been equilibrated with 50 mM HEPES, pH 7.4 containing 0.3 M NaCl and 6 mM CaCl$_2$. The column was then washed with the equilibration buffer containing 1 M NaCl. Retained proteins were eluted with 50 mM HEPES, pH 7.4, 3 M NaCl, 2 M urea, 6 mM CaCl$_2$. The elution peak was concentrated and dialyzed against 50 mM HEPES, pH 7.4 containing 0.3 M NaCl, 6 mM CaCl$_2$. The preparation was centrifuged at 3000 g for 10 minutes. Brij 35 (Sigma, Madison, Wis.) was added to the supernatant to a final concentration of 0.02%. This preparation was used for screening.

Example XII

Isolation of Collagenase Enzymes

The catalytic domain of human collagenase-1 was expressed as a fusion protein with ubiquitin in *E. Coli* as described in Gehring, E. R. et al., *J. Biol. Chem.*, 270, 22507, (1995). After purification of the fusion protein, the collagenase-1 catalytic domain was released by treatment with 1 mM of aminophenylmercuric acetate (APMA) for 1 hour at 37° C. and then purified by zinc chelate chromatography.

Human collagenase-2 and gelatinase B were isolated in active form from buffy coats as described in Mookhtiar, K. A. et al., *Biochemistry*, 29, 10620, (1990).

The propeptide and catalytic domain portion of human collagenase-3 was expressed in *E. Coli* as an N-terminal fusion protein with ubiquitin. After purification, the catalytic domain was released by treatment with 1 mM APMA for 1 hour at 37° C., and then purified by zinc chelate chromatography.

Rat collagenase-3 was purified in active form from the culture media of uterine smooth muscle cells as described in Roswit, W. T. et al., *Arch. Biochem. Biophys.*, 225, 285–295 (1983).

Example XIII

Inhibition of Procollagen C-Proteinase Activity

The ability of the compounds to inhibit PCP has been demonstrated in the following in vitro assays utilizing a synthetic peptide as the substrate.

Assay A

A continuous assay was performed using 20 μM substrate (Dabcyl-Pro-Tyr-Tyr-Gly-Asp-Glu-Pro-n-Leu-Edans) (SEQ ID NO:6). The final assay conditions were 20 μM substrate, 50 mM HEPES pH 7.5, 50 mM NaCl, 3% DMSO, 37° C. and PCP enzyme. Product formation was monitored by fluorescence spectroscopy, Ex.=335 nm, Em.=490 nm. The IC$_{50}$ was calculated from plots of the initial velocity vs. compound concentration.

Assay B

Eighty μL of buffer A (20 mM HEPES) containing the desired concentrations of the test compound in DMSO or carrier vehicle was mixed with 10 μL of approx. 1 mg/mL PCP enzyme and 10 μL of 0.1 mM substrate both in 20 mM HEPES. The contents are mixed, incubated at room temperature for 1–2 hours and fluorescent readings taken with a Victor plate reader (Ex. 405 nm, Em. 460 nM at 2000–40, 000 lamp energy, 0.1–1 sec/well). The substrate was DACM-Cys-Pro-Tyr-Gly-Asp-Glu-Pro-nLeu-Lys-FITC-OH. (SEQ ID NO:7) (DACM=dimethylaminocoumarylmaleimide, FITC=fluorescein isothiocyanate). The IC$_{50}$ was calculated from plots of the initial velocity vs. compound concentration.

Additional in vitro assays using native procollagen as the substrate may also be used and these assays are described in more detail in WO 97/05865 ("C-Proteinase Inhibitors for the Treatment of Disorders Relating to the Overproduction of Collagen"), published Feb. 20, 1997.

The compounds in Tables I–III, V and VI had IC$_{50}$'s in the range of 0.02 to 200 μM.

Example XIV

Measurement of Collagenase Activity

The collagenase-1, collagenase-2 and collagenase-3 inhibitory activity of compounds of this invention in vitro was determined based on the hydrolysis of MCA-Pro-Leu-Gly-Leu-DPA-Ala-Arg-NH$_2$ (SEQ ID NO:8) (Bachem, Inc.) at 37° C. as described in Knight, C. G., et al., *FEBS Lett.*, 296(3): 263–266 (1992).

The collagenase enzyme was diluted with assay buffer (50 mM Tricine pH 7.5, 200 mM NaCl, 10 mM CaCl$_2$, and 0.005% Brij-35) containing 10 μmole of above substrate dissolved in DMSO. Compounds of the invention dissolved in DMSO or only DMSO (control samples) were added such that the final DMSO concentration in all assays was 2.5%. The fluorescence changes hi were monitored with a Perkin-Elmer LS-50B fluorimeter using an excitation wavelength of 328 nm and an emission wavelength of 393 nm.

The compounds in Table IV had IC$_{50}$'s in the range of 10–1000 μM.

Selected compounds from Tables I–VI were 10–1000 more selective for PCP inhibition than for the human collagenase enzymes.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A compound selected from the group of compounds represented by Formula (I):

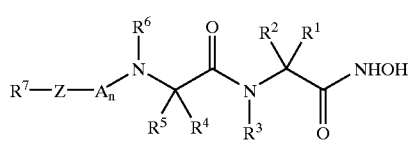

wherein:

$R^1$ and $R^4$ are, independently of each other, hydrogen or alkyl;

$R^2$ is:

(i) cycloalkyl, cycloalkylalkyl, aryl, aralkyl, aralkenyl, heteroaryl, heteroaralkyl, heteroaralkenyl, heterocyclo or heterocycloalkyl; provided that $R^2$ does not contain an imidazole group or (ii) -(alkylene)-$B^1$—X where $B^1$ is —O—, —$NR^8$—, —$S(O)_{0-2}$, —C═O, —$CONR^8$—, —$NR^8CO_2$—, $NR^8SO_2$— or —C(═$NR^8$)$NR^8SO_2$-(where $R^8$ is H or alkyl), and X is cycloalkyl, cycloalkylalkyl, aryl, aralkyl, heteroaryl, or heteroaralkyl; or (iii) -(alkylene)-$B^1$—X where $B^1$ is —$NR^8CO$— (where $R^8$ is H or alkyl), and X is cycloalkyl, cycloalkylalkyl, aryl, aralkyl, heteroaryl or heteroaralkyl; or (iv) $R^2$ and $R^3$ form an alkylene or heteroalkylene chain; with the proviso that $R^2$ does not contain an imidazole group, $R^3$ is hydrogen or alkyl;

$R^6$ is hydrogen, alkyl, cycloalkyl, cycloalkylalkyl, aryl, aralkyl, heteroaryl or heteroaralkyl;

$R^5$ is:
   (i) hydrogen, alkyl, cycloalkyl, cycloalkylalkyl, aryl, aralkyl, aralkenyl, heteroaryl, heteroaralkyl, heteroaralkenyl, heterocycloalkyl, heteroalkyl, or -(alkylene)-C(O)—$X^1$ where $X^1$ is alkyl, hydroxy, alkoxy, aryl, aralkyl, aryloxy, aralkyloxy, heteroaryl, heteroaryloxy, heteroaralkyloxy or NR'R" (where R' and R" are independently H or alkyl, or R' and R" form an alkylene chain); or
   (ii) $R^5$ and $R^4$ form an alkylene chain; or
   (iii) $R^5$ and $R^6$ form an alkylene chain;
n is 0 or 1;
A is —N($R^{10}$)—($CH_2$)$_m$—CH($R^9$)—C(=O)— wherein:
   m is an integer from 0–5 inclusive;
   $R^9$ is hydrogen, alkyl, cycloalkyl, cycloalkylalkyl, aryl, aralkyl, heteroaryl, heteroaralkyl, heterocycloalkyl, heteroalkyl, or -(alkylene)-C(O)—$X^1$ where $X^1$ is alkyl, hydroxy, alkoxy, aryl, aralkyl, aryloxy, aralkyloxy, heteroaryl, heteroaryloxy, heteroaralkyloxy or NR'R" (where R' and R" are independently H or alkyl, or R' and R" form an alkylene chain); and
   $R^{10}$ is hydrogen, alkyl, aralkyl or heteroaralkyl;
Z is Y—$B^2$ wherein:
   Y is alkylene or a bond; and
   $B^2$ is —CO—, —OC(O)—,
with the proviso that when $R^2$ is benzyl, 4-hydroxybenzyl, phenyl, or phenethyl, then Z is not —OC(O)—;
$R^7$ is cycloalkyl, cycloalkylalkyl, aryl, aralkyl, heteroaryl or heteroaralkyl;
or a pharmaceutically acceptable salt, prodrug, or isomer thereof.

2. The compound of claim 1 wherein:
n is 0.
3. The compound of claim 2 wherein $R^3$ and $R^6$ are hydrogen.
4. The compound of claim 3, wherein:
$R^2$ is aralkyl or heteroaralkyl.
5. The compound of claim 4, wherein Z is —OC(O)—.
6. The compound of claim 5 wherein $R^2$ is substituted benzyl or optionally substituted heteroarylmethyl, wherein said substituted benzyl is not a 4-hydroxybenzyl.
7. The compound of claim 6 wherein, $R^2$ is 4-t-butoxybenzyl, 3-chlorobenzyl, 3-indolyl methyl, 2-thienylmethyl, or 4-thiazolylmethyl.
8. The compound of claim 7 wherein $R^2$ is 4-thiazolylmethyl.
9. The compound of claim 8 wherein:
$R^7$ is aryl, aralkyl, heteroaryl or heteroaralkyl.
10. The compound of claim 8 wherein:
Z is —C(O)O— and $R^7$ is optionally substituted benzyl.
11. The compound of claim 10, wherein:
$R^1$ and $R^4$ are hydrogen and $R^5$ is alkyl.
12. The compound of claim 11 wherein $R^5$ is a 1-methylpropyl, wherein the carbon bearing methyl is of the "S" configuration, and wherein the carbon bearing $R^5$ is also of the "S" configuration.
13. The compound of claim 3, wherein:
$R^2$ is (alkylene)-$B^1$—X where $B^1$ is —O—, —$NR^8$—, —S(O)$_{0-2}$, —C=O, —$CONR^8$—, —$NR^8CO_2$—, —$NR^8SO_2$— or —C(=$NR^8$)$NSO_2$-(where $R^8$ is H or alkyl), and X is cycloalkyl, cycloalkylalkyl, aryl, aralkyl, heteroaryl, or heteroaralkyl.
14. The compound of claim 13, wherein Z is —OC(O)—.
15. The compound of claim 14, wherein $R^2$ is $CH_2$—$B^1$—X, and $B^1$ is —$NHCO_2$— and X is benzyl.
16. The compound of claim 15 wherein:
$R^7$ is aryl or aralkyl.
17. The compound of claim 16, wherein:
$R^1$ and $R^4$ are hydrogen and $R^5$ is alkyl.
18. The compound of claim 17, wherein $R^5$ is 1-methylpropyl, wherein the carbon bearing methyl is of the "S" configuration, and wherein the carbon bearing $R^5$ is also of the "S" configuration.
19. The compound of claim 1 wherein:
n is 1.
20. The compound of claim 19 wherein m is 0 and $R^3$ and $R^6$ are hydrogen.
21. The compound of claim 20, wherein:
$R^2$ is aralkyl or heteroaralkyl.
22. The compound of claim 21, wherein Z is —OC(O)—.
23. The compound of claim 22, wherein:
$R^2$ is optionally substituted benzyl or heteroarylmethyl.
24. The compound of claim 22, wherein $R^2$ is 4-t-butoxybenzyl, 3-chlorobenzyl, 3-indolyl methyl, 2-thienylmethyl, or 4-thiazolylmethyl.
25. The compound of claim 24 wherein $R^2$ is 4-thiazolylmethyl.
26. The compound of claim 25 wherein:
$R^7$ is aryl, aralkyl, heteroaryl or heteroaralkyl.
27. The compound of claim 26 wherein:
Z is —C(O)O— and $R^7$ is benzyl.
28. The compound of claim 27, wherein:
$R^1$ and $R^4$ are hydrogen and $R^5$ is alkyl.
29. The compound of claim 28, wherein $R^5$ is 1-methylpropyl, wherein the carbon bearing methyl is of the "S" configuration, and wherein the carbon bearing $R^5$ is also of the "S" configuration.
30. The compound of claim 20, wherein:
$R^2$ is (alkylene)-$B^1$—X where $B^1$ is —O—, —$NR^8$—, —S—, —C=O, —$CONR^8$—, —$NR^8CO_2$—, —$NSO_2$— or —C(=$NR^8$)$NSO_2$-(where $R^8$ is H or alkyl), and X is cycloalkyl, cycloalkylalkyl, aryl, aralkyl, heteroaryl, or heteroaralkyl.
31. The compound of claim 30, wherein Z is —OC(O)—.
32. The compound of claim 31, wherein $R^2$ is $CH_2$—$B^1$—X, and
$B^1$ is —$NHCO_2$— and X is benzyl.
33. The compound of claim 32 wherein:
$R^7$ is aryl or aralkyl.
34. The compound of claim 33, wherein:
$R^1$ and $R^4$ are hydrogen and $R^5$ is alkyl.
35. The compound of claim 34 wherein $R^5$ is 1-methylpropyl, wherein the carbon bearing methyl is of the "S" configuration, and wherein the carbon bearing $R^5$ is also of the "S" configuration.
36. A composition comprising the compound of claim 1 and a pharmaceutically acceptable excipient.
37. A mixture consisting of a compound according to claim 1, and one or more stereoisomers thereof.
38. A method of inhibiting procollagen C-proteinase comprising contacting procollagen C-proteinase with a compound according to claim 1 for a time and under conditions effective to inhibit procollagen C-proteinase.
39. A method of inhibiting procollagen C-proteinase in a mammal comprising administering to a mammal in need of procollagen C-proteinase inhibition a compound according to claim 1 for at time and under conditions effective to inhibit procollagen C-proteinase.
40. A method of inhibiting procollagen C-proteinase in a mammal afflicted with a fibrotic disease comprising administering to said mammal a compound according to claim 1 for a time and under conditions effective to inhibit procollagen C-proteinase.

41. A method of inhibiting deposition of collagen fibers in a mammal afflicted with a fibrotic disease comprising administering to said mammal a compound according to claim 1 for a time and under conditions effective to inhibit procollagen C-proteinase.

* * * * *

SEQUENCE LISTING

```
<160> NUMBER OF SEQ ID NOS: 8

<210> SEQ ID NO 1
<211> LENGTH: 122
<212> TYPE: DNA
<213> ORGANISM: Artificial Sequence
<220> FEATURE:
<223> OTHER INFORMATION: pcr primer

<400> SEQUENCE: 1
gcgcgcggta cccgccccgc cagcatgccc ggcgtggccc gcctgccgct gctgctcggg     60
ctgctgctgc tcccgcgtcc cggccggccg ctggacttgg ccgactacac ctatgacctg    120
gc                                                                   122

<210> SEQ ID NO 2
<211> LENGTH: 59
<212> TYPE: DNA
<213> ORGANISM: Artificial Sequence
<220> FEATURE:
<223> OTHER INFORMATION: pcr primer

<400> SEQUENCE: 2
ccgctcgagc ctcactgggg ggtccggttt cttttctgca ctcggaattt gagctggtg      59

<210> SEQ ID NO 3
<211> LENGTH: 23
<212> TYPE: DNA
<213> ORGANISM: Artificial Sequence
<220> FEATURE:
<223> OTHER INFORMATION: pcr primer

<400> SEQUENCE: 3
gacgaagagg acctgagggc ctt                                             23

<210> SEQ ID NO 4
<211> LENGTH: 21
<212> TYPE: DNA
<213> ORGANISM: Artificial Sequence
<220> FEATURE:
<223> OTHER INFORMATION: pcr primer
```

```
<400> SEQUENCE: 4
ttcctggaac tgcagctttg a                                          21

<210> SEQ ID NO 5
<211> LENGTH: 25
<212> TYPE: DNA
<213> ORGANISM: Artificial Sequence
<220> FEATURE:
<223> OTHER INFORMATION: pcr primer

<400> SEQUENCE: 5
tgccgtctga gatccacagc ctgct                                      25

<210> SEQ ID NO 6
<211> LENGTH: 8
<212> TYPE: PRT
<213> ORGANISM: Artificial Sequence
<220> FEATURE:
<223> OTHER INFORMATION: synthetic peptide

<400> SEQUENCE: 6

Pro Tyr Tyr Gly Asp Glu Pro Leu
 1               5

<210> SEQ ID NO 7
<211> LENGTH: 9
<212> TYPE: PRT
<213> ORGANISM: Artificial Sequence
<220> FEATURE:
<223> OTHER INFORMATION: synthetic peptide

<400> SEQUENCE: 7

Cys Pro Tyr Gly Asp Glu Pro Leu Lys
 1               5

<210> SEQ ID NO 8
<211> LENGTH: 7
<212> TYPE: PRT
<213> ORGANISM: Artificial Sequence
<220> FEATURE:
<223> OTHER INFORMATION: synthetic peptide
<223> OTHER INFORMATION: Xaa = DPA

<400> SEQUENCE: 8

Arg Ala Xaa Leu Gly Leu Pro
 1               5
```